US012755405B2

(12) United States Patent
Woo et al.

(10) Patent No.: US 12,755,405 B2
(45) Date of Patent: Oct. 6, 2026

(54) 2D-3D IMAGE REGISTRATION METHOD AND MEDICAL OPERATING ROBOT SYSTEM FOR PERFORMING THE SAME

(71) Applicant: CUREXO, INC., Seoul (KR)

(72) Inventors: Dong Gi Woo, Seoul (KR); Sung Teac Hwang, Seoul (KR)

(73) Assignee: CUREXO, INC., Seoul (KR)

( * ) Notice: Subject to any disclaimer, the term of this patent is extended or adjusted under 35 U.S.C. 154(b) by 309 days.

(21) Appl. No.: 18/498,505

(22) Filed: Oct. 31, 2023

(65) Prior Publication Data

US 2024/0144498 A1 May 2, 2024

(30) Foreign Application Priority Data

Nov. 2, 2022 (KR) ........................ 10-2022-0144585

(51) Int. Cl.

| | |
|---|---|
| ***G06T 7/33*** | (2017.01) |
| ***A61B 34/10*** | (2016.01) |
| ***A61B 34/20*** | (2016.01) |
| ***A61B 34/30*** | (2016.01) |
| ***A61B 90/00*** | (2016.01) |
| ***G06T 7/00*** | (2017.01) |

(52) U.S. Cl.

CPC ................ *G06T 7/33* (2017.01); *A61B 34/20* (2016.02); *A61B 34/30* (2016.02); *G06T 7/0012* (2013.01);

(Continued)

(58) Field of Classification Search

CPC .................... A61B 2090/367; A61B 2034/107

See application file for complete search history.

(56) References Cited

U.S. PATENT DOCUMENTS 7,204,640 B2 * 4/2007 Fu .......................... G01N 23/04 378/65
7,623,623 B2 11/2009 Raanes et al.

(Continued)

FOREIGN PATENT DOCUMENTS

EP 3306567 A1 4/2018
EP 3936079 A1 1/2022

(Continued)

OTHER PUBLICATIONS

Montufar, J. Jesus et al., "Perspective and orthogonal CBCT/CT digitally reconstructed radiographs compared to conventional cephalograms", Biomedical Engineering and Science (BIOENG'16), ISBN 1-60132-429-4, CSREA Press, 2016.

(Continued)

*Primary Examiner* — Peter K Huntsinger

(74) *Attorney, Agent, or Firm* — Bridgeway IP Law Group, PLLC; Jihun Kim

(57) ABSTRACT

An image registration method and apparatus, a medical operating robot system using the same, and a computer program medium are described. The image registration method includes: extracting digitally reconstructed radiograph (DRR) images in an anterior-posterior (AP) direction and a lateral-lateral (LL) direction from the 3D image; acquiring 2D images for an AP image and an LL image of the patient's surgical; determining a first rotation angle between a reference position and a predetermined first reference position of the patient's surgical site corresponding to the first reference position of the AP image or LL image; determining a second rotation angle between the reference position and the second reference position of the AP image or LL image corresponding to the reference position; and determining a transformation relationship (Continued)

between the 2D image and the DRR image based on the first and second rotation angles.

13 Claims, 22 Drawing Sheets

(51) Int. Cl.

| | |
|---|---|
| ***G06T 17/00*** | (2006.01) |
| ***G06V 10/25*** | (2022.01) |
| ***G06V 10/82*** | (2022.01) |

(52) U.S. Cl.

CPC .............. *G06T 17/00* (2013.01); *G06V 10/25* (2022.01); *G06V 10/82* (2022.01); *A61B 2034/107* (2016.02); *A61B 2034/2065* (2016.02); *A61B 2090/367* (2016.02); *G06T 2207/10076* (2013.01); *G06T 2207/10116* (2013.01); *G06T 2207/20084* (2013.01); *G06T 2207/30012* (2013.01)

(56) References Cited

U.S. PATENT DOCUMENTS

| | | | | |
|---|---|---|---|---|
| 10,621,738 | B2 | 4/2020 | Miao et al. | |
| 2021/0038181 | A1* | 2/2021 | Schweizer ............. | A61B 6/466 |
| 2021/0137634 | A1 | 5/2021 | Lang | |
| 2021/0196402 | A1* | 7/2021 | Yin ......................... | A61B 17/34 |
| 2022/0039875 | A1 | 2/2022 | Choi et al. | |
| 2023/0230243 | A1* | 7/2023 | Sun ......................... | A61B 6/547<br>382/128 |
| 2023/0240628 | A1* | 8/2023 | Cohen .................. | A61B 6/4441<br>382/128 |

FOREIGN PATENT DOCUMENTS

| | | | |
|---|---|---|---|
| KR | 10-2017-0030687 | A | 3/2017 |
| KR | 10-2203544 | B1 | 1/2021 |
| KR | 10-2394901 | B1 | 5/2022 |
| WO | 2017/160651 | A1 | 9/2017 |
| WO | 2017/189881 | A1 | 11/2017 |
| WO | 2019/010203 | A1 | 1/2019 |

OTHER PUBLICATIONS

Chang, Chih-Ju et al., “Registration of 2D C-Arm and 3D CT Images for a C-Arm Image-Assisted Navigation System for Spinal Surgery,” Applied Bionics and Biomechanics, 2015, Article ID 478062, 9 pages, vol. 2015, Hindawi Publishing Corporation, United Kingdom.

* cited by examiner

2D-3D IMAGE REGISTRATION METHOD AND MEDICAL OPERATING ROBOT SYSTEM FOR PERFORMING THE SAME

CROSS-REFERENCE TO RELATED APPLICATION

This application is based on and claims priority under 35 U.S.C. § 119 to Korean Patent Application No. 10-2022-0144585 filed on Nov. 2, 2022 in the Korean Intellectual Property Office, the disclosure of which is incorporated by reference herein in its entirety.

BACKGROUND

Field

The disclosure relates to image registration, and more particularly to an image registration method and a medical operating robot system for performing the same, in which operation planning and navigation information is displayed on a desired image through registration between a pre-operative 3D image and an intra-operative 2D image.

Description of the Related Art

Operative navigation technology based on image registration has been used to assist a doctor in an operation.

Before starting an operation, a doctor makes an operation plan for determining an optimal implant product, a surgical position for an implant, a trajectory of a surgical instrument, or the like based on a 3D computed tomography (CT) image of a surgical site. During the operation, the doctor operates the surgical instrument while comparing and checking the real-time positions of the surgical instrument, the implant, etc. corresponding to operating status with the operation plan to ensure that the operation is proceeding well according to the operation plan.

While the operation plan is made based on a 3D image from a CT scanner mainly used before the operation, the operating status is provided based on a 2D image from an imaging device, e.g., a C-arm mainly used during the operation because the surgical instrument and the C-arm are registered to the same coordinate system during the operation.

Therefore, 3D-2D image registration is needed to provide integrated information about the operation plan and the operating status, and it is required to improve the accuracy of the image registration and shorten the processing time of the image registration for a successful operation.

However, a patient's movement may cause twist of his/her spine, left and right asymmetry of his/her pelvis, etc., thereby resulting in an inconsistent image whenever an image is acquired. Therefore, minute changes in pose, due to the patient's movement, in particular, due to joint rotation rather than position change should be quickly processed to perform the image registration, but image registration technology reflecting such change in pose caused by the joint rotation has not been utilized in the field of conventional navigation technology.

DOCUMENTS OF RELATED ART

Patent Document (Patent Document 1) Korean Patent No. 2203544
(Patent Document 2) Korean Patent No. 2394901

SUMMARY

Accordingly, an aspect of the disclosure is to provide an image registration method capable of quick image registration processing and compensation for movement due to joint rotation, and a medical operating robot system, image registration apparatus, and computer program medium for performing the same.

According to an embodiment of the disclosure, there is provided an image registration method, steps of which are performed by an image registration apparatus including a processor, includes: acquiring a 3D image of a patient's surgical site from a 3D imaging apparatus before an operation; extracting digitally reconstructed radiograph (DRR) images in an anterior-posterior (AP) direction and a lateral-lateral (LL) direction from the 3D image; acquiring 2D images for an AP image and an LL image of the patient's surgical site from a 2D imaging apparatus during an operation; determining a first rotation angle between a reference position and a predetermined first reference position of the patient's surgical site corresponding to the first reference position of the AP image or LL image, based on a first rotation axis passing through a predetermined first origin and parallel to a cross product vector of first normal vectors for planes of the AP image and the LL image, from a geospatial relationship between a source and a detector with respect to the DRR image; determining a second rotation angle between the reference position and the second reference position of the AP image or LL image corresponding to the reference position, based on a second rotation axis passing through a predetermined second origin and parallel to a cross product vector of second normal vectors for planes of the AP image and the LL image, from a geospatial relationship between a source and a detector with respect to the 2D image; and determining a transformation relationship between the 2D image and the DRR image based on the first and second rotation angles, from the geospatial relationships between the sources and the detectors of the DRR and 2D images.

Here, the first reference position and the second reference position may include a center of the AP image or LL image for each of the 2D image and the DRR image, or a line or plane including the center.

The image registration method may further include performing operation planning based on the 3D image by the image registration apparatus, wherein the first origin for the DRR image is determined based on a relative relationship of a trajectory of a surgical instrument for mounting an implant or a mounting position of the implant applied to the operation planning. Further, the reference position for the DRR image or 2D image may be determined based on a user's input.

In the image registration method, the geospatial relationship between the source and the detector for the DRR image may include an orthogonal projection relationship, and the geospatial relationship between the source and the detector for the 2D image may include a perspective projection relationship.

In addition, the image registration method may further include: determining a first volume of interest where planes intersect as the plane of the AP image and the plane of the LL image are moved in directions of the first normal vectors, from the geospatial relationship between the source and the detector for the DDR image; and determining a second volume of interest where planes intersect as the AP image and the LL image are moved in directions of the second normal vectors within a perspective projection range, wherein the geospatial relationship between the source and the detector for the 2D image includes a perspective projection relationship. Here, the first origin may include a center of the first volume of interest, and the second origin may include a center of the second volume of interest.

Further, the image registration method may further include: determining a first region of interest for each of the AP image and LL image of the DRR image; and determining a second region of interest corresponding to the first region of interest for each of the AP image and LL image of the 2D image, wherein the first reference position is positioned within the first region of interest, and the second reference position is positioned within the second region of interest. Further, the method may further include: determining a first volume of interest where planes intersect as a region of interest on the AP image and a region of interest on the LL image are moved in directions of the first normal vectors, from the geospatial relationship between the source and the detector for the DDR image; and determining a second volume of interest where planes intersect as a region of interest on the AP image and a region of interest on the LL image are moved in directions of the second normal vectors within a perspective projection relationship, wherein the geospatial relationship between the source and the detector for the 2D image includes a perspective projection relationship, wherein the first origin may include a center of the first volume of interest, and the second origin may include a center of the second volume of interest.

Further, in the image registration method, the first origin may include a center between target positions of a patient's spine pedicle screws, and wherein the first rotation angle may include an angle formed between a line segment that connects the first origin and a midpoint between the pedicle screw entry points, and the first normal vector that passes through the center of the first volume of interest, with respect to the first origin.

In addition, each first region of interest for the AP image and LL image of the DRR image may include a rectangle, and regarding the DRR image, the image registration method may include: a first step of calculating first intersection points between an epipolar line on the LL image for the vertices of the region of interest on the AP image and a midline connecting midpoints of an outer circumference or lateral sides of a region of interest on the LL image; a second step of acquiring four reconstructed points by orthogonal projection of the first intersection points to the normal vectors from the vertices of the region of interest on the AP image; a third step of calculating second intersection points between an epipolar line on the AP image for the vertices of the region of interest on the LL image and a midline connecting midpoints of an outer circumference or lateral sides of a region of interest on the AP image; a fourth step of acquiring four reconstructed points by orthogonal projection of the second intersection points to the normal vectors from the vertices of the region of interest on the LL image; and a fifth step of calculating a first volume of interest in a hexahedron formed based on eight reconstructed points obtained through the first to fourth steps.

Further, the determining the second volume of interest may include: regarding the 2D image, a first step of calculating first intersection points between an epipolar line on the LL image for the vertices of the region of interest on the AP image and a midline connecting midpoints of an outer circumference or lateral sides of a region of interest on the LL image; a second step of acquiring four reconstructed points by perspective projection of the first intersection points to perspective projection vector from the vertices of the region of interest on the AP image toward the source; a third step of calculating second intersection points between an epipolar line on the AP image for the vertices of the region of interest on the LL image and a midline connecting midpoints of an outer circumference or lateral sides of a region of interest on the AP image; a fourth step of acquiring four reconstructed points by perspective projection of the second intersection points to the perspective projection vectors from the vertices of the region of interest on the LL image toward the source; and a fifth step of calculating a second volume of interest in a hexahedron based on eight reconstructed points obtained through the first to fourth steps.

Further, according to another embodiment of the disclosure, there is provided an image registration method, steps of which are performed by an image registration apparatus including a processor, the method including: acquiring a 3D image of a patient's surgical site from a 3D imaging apparatus before an operation; extracting DRR images in an AP direction and a LL direction from the 3D image; acquiring 2D images for an AP image and an LL image of the patient's surgical site from a 2D imaging apparatus during an operation; determining a first region of interest for each of the AP image and the LL image of the DRR image; determining a second region of interest corresponding to the first region of interest with respect to each of the AP image and the LL image of the 2D image; determining a first volume of interest formed by intersection of planes upon parallel translation of a region of interest on the AP image and a region of interest on the LL image in a direction of a first normal vector to the planes of the AP image and the LL image, from a geospatial relationship between a source and a detector with respect to the DRR image; determining a second volume of interest formed by intersection of planes upon translation of a region of interest on the AP image and a region of interest on the LL image in a direction of a second normal vector to the AP image and the LL image of the 2D image within a perspective projection range, wherein the geospatial relationship between the source and the detector for the 2D image includes a perspective projection relationship; determining first displacement between a first reference position within the first volume of interest corresponding to a predetermined first reference position in the first region of interest and a predetermined reference position corresponding to the first reference position; determining second displacement between the reference position and a second reference position within the second volume of interest for a predetermined second reference position within the second region of interest corresponding to the reference position; and determining a transformation relationship to minimize a Euclidean distance between vertices of the first region of interest and vertices of the second region of interest based on a transformation relationship, as the transformation relationship between the 2D image and the DRR image is determined from geospatial relationships for the source and the detector of each of the DRR image and the 2D image, based on the first displacement and the second displacement.

Here, the determining the first displacement may include determining a first rotation angle based on an angle between the reference position and the first reference position, with respect to a first rotation axis passing through a predetermined first origin and parallel to a cross product vector of the first normal vectors for planes of the AP image and the LL image; and the determining the second displacement may include determining a second rotation angle based on an angle between the reference position and the second reference position, with respect to a second rotation axis passing through a predetermined second origin and parallel to a cross product vector of the second normal vectors for planes of the AP image and the LL image.

In addition, the determining the first and second volumes of interest may include forming a polyhedron by projecting an epipolar line of vertices of the first and second regions of interest to the first and second normal vectors.

Further, according to still another embodiment of the disclosure, there is provided an image registration apparatus includes a processor to perform the foregoing image registration method.

Further, according to still another embodiment of the disclosure, there is provided a medical operating robot system including: a 2D imaging apparatus configured to acquire a 2D image of a patient's surgical site during an operation; a robot arm including an end effector to which a surgical instrument is detachably coupled; a position sensor configured to detect a real-time position of the surgical instrument or the end effector; a controller configured to control the robot arm based on predetermined operation planning; a display; and a navigation system configured to display the planning information about the surgical instrument or implant on a 2D image acquired during an operation or display the real-time position of the surgical instrument or implant on the 2D image or a 3D image acquired before the operation, through the display, by performing the foregoing image registration method.

Further, according to still another embodiment of the disclosure, there is provided a computer program medium storing software to perform the foregoing image registration method.

BRIEF DESCRIPTION OF THE DRAWINGS

The above and/or other aspects will become apparent and more readily appreciated from the following description of embodiments, taken in conjunction with the accompanying drawings, in which.

DETAILED DESCRIPTION OF EMBODIMENTS

Below, embodiments of the disclosure will be described with reference to the accompanying drawings.

Figure 1:
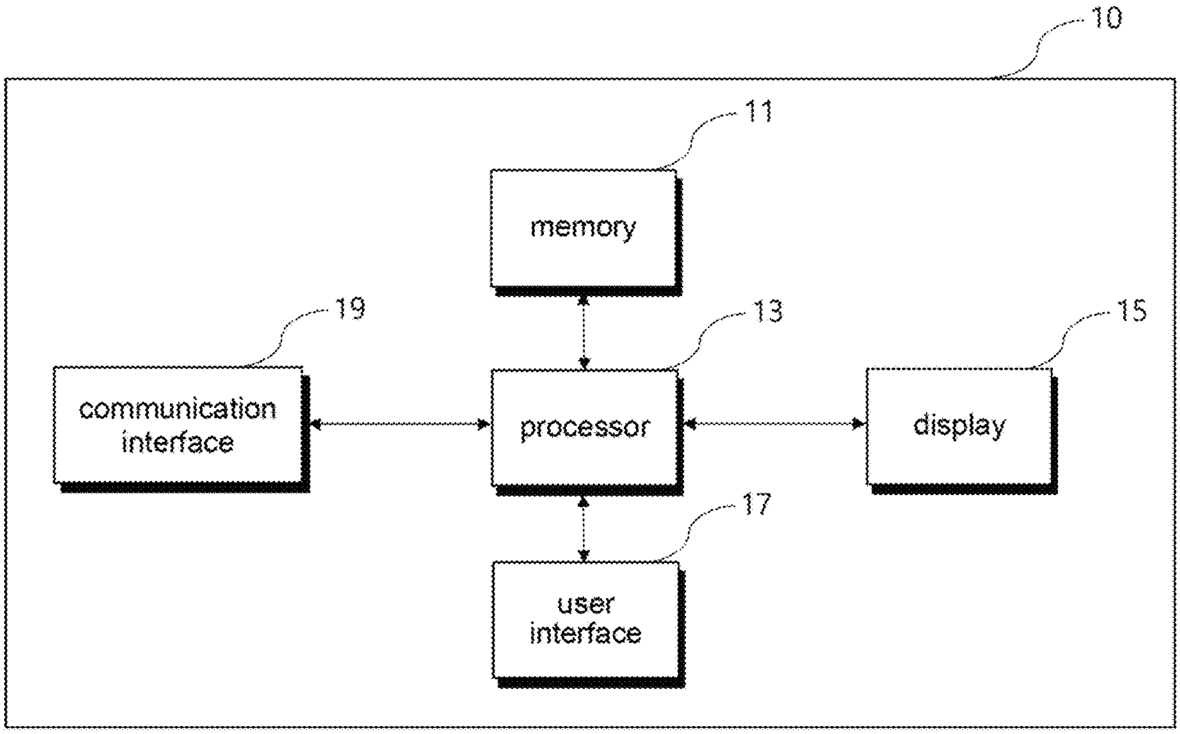
FIG. 1 is a block diagram of an image registration apparatus according to an embodiment of the disclosure.

FIG. 1 is a block diagram schematically showing the configuration of an image registration apparatus 10 for performing image registration according to an embodiment of the disclosure. AS an electronic apparatus capable of performing the image registration, the image registration apparatus 10 refers to a computing apparatus such as a computer, a notebook computer, a laptop computer, a tablet personal computer (PC), a smartphone, a mobile phone, a personal media player (PMP), and a personal digital assistant (PDA). An image registration method according to an embodiment of the disclosure may be applied to medical image processing software such as medical navigation software. The image registration apparatus 10 according to an embodiment of the disclosure may execute image processing software such as an operation plan or planning as well as the medical navigation software.

Referring to FIG. 1, the image registration apparatus 10 according to an embodiment of the disclosure includes a memory 11 for storing data and a program code, and a processor 13 for executing the data and the program code.

The memory 11 refers to a computer-readable recording medium, and stores at least one computer program code to be performed by the processor 13. Such a computer program code may be loaded from a floppy drive, a disk, a tape, a digital versatile disc (DVD)/compact disc read only memory (CD-ROM) drive, a memory card, etc., which are separated from the memory 11, into the memory 11. The memory 11 may store software for the image registration, a patient's medical image or data, etc.

The processor 13 is to execute and process a computer program instruction through basic logic, calculations, operations, etc., and the computer program code stored in the memory 11 is loaded into and executed by the processor 13.

The processor 13 may execute an algorithm stored in the memory 11 to perform a series of 2D-3D image registration.

As shown in FIG. 1, the image registration apparatus 10 according to an embodiment of the disclosure may further include a display 15 for displaying data and images, a user interface 17 for receiving a user's input, and a communication interface 19 for interworking with the outside. The user interface 17 may for example include input devices such as a microphone, a keyboard, a mouse, or a foot pad.

Below, the image registration method performed by the image registration apparatus 10 (or the processor 13) according to an embodiment of the disclosure will be described.

Figure 2:
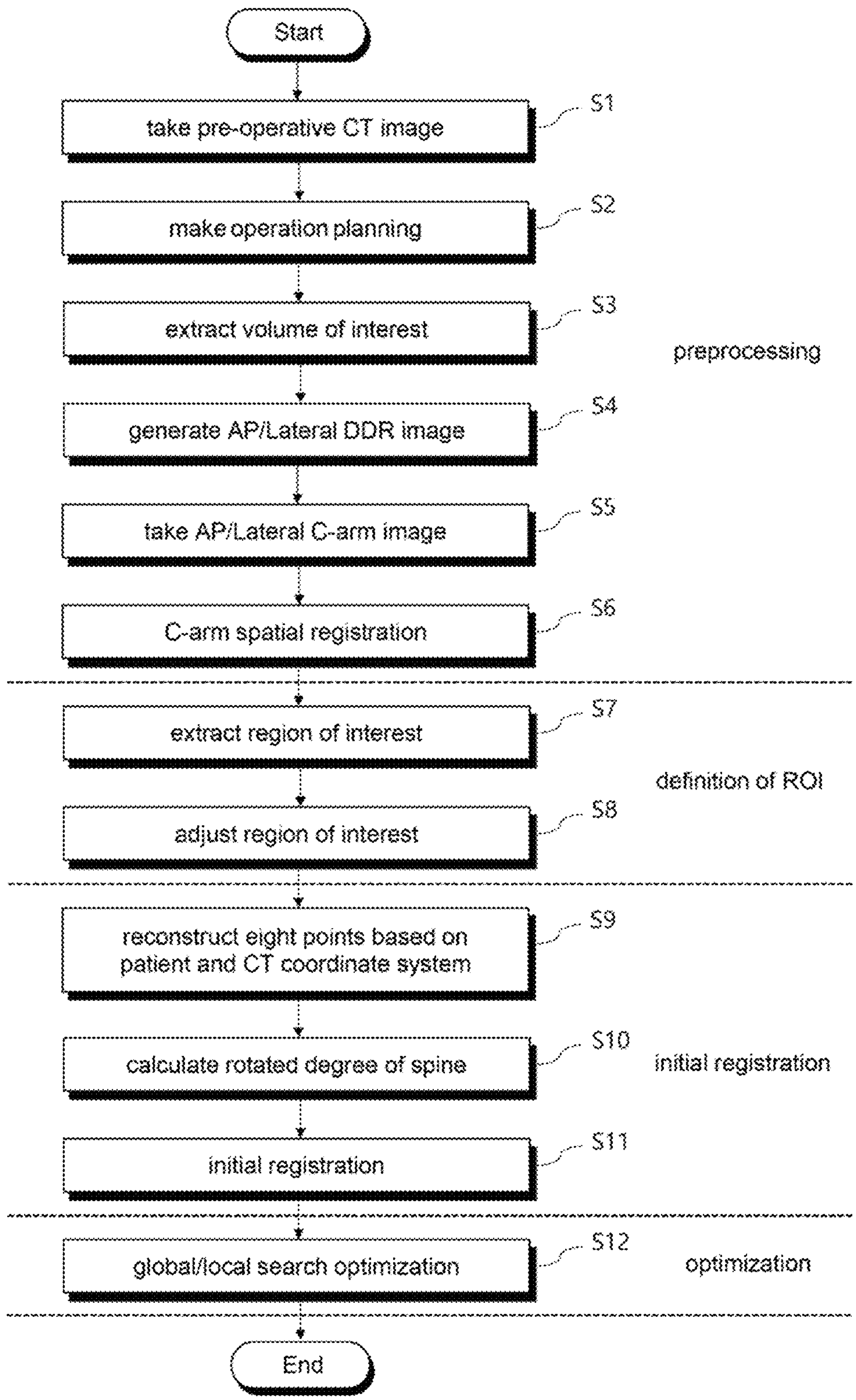
FIG. 2 is a flowchart of an image registration method according to an embodiment of the disclosure.

FIG. 2 is a flowchart of the image registration method according to an embodiment of the disclosure, and FIGS. 3 to 14 are schematic diagrams illustrating the steps in the flowchart of FIG. 2.

Referring to FIG. 2, the image registration method according to an embodiment of the disclosure includes pre-operative planning steps.

First, a 3D image is acquired by taking a pre-operative a computed tomography (CT) image for a patient's surgical site through an imaging apparatus (S1). Here, another imaging apparatus for acquiring the 3D image, e.g., a magnetic resonance imaging (MRI), etc., may be used as an alternative to the CT, and the disclosure is not limited to a specific imaging apparatus.

A doctor uses operation planning software to make an operation plan for a patient's 3D image (S2). For example, in the case of an operation of inserting and fixing a screw into a pedicle during a spinal operation, the selection of a screw product based on the diameter, length, material, etc. of the screw, a pedicle entry point for the screw, a target where the end of the screw is settled, etc. may be set and displayed on the 3D image. Such planning software is provided by many companies in various operative fields.

Next, the image registration apparatus 10 extracts a volume of interest with respect to the surgical site for which the operation plan is established (S3). Such extraction may be automatically performed by an automated algorithm with respect to the position of a planning object, e.g., the screw displayed on the 3D image, or may be performed as large as a given volume boundary is adjusted by a doctor in person.

Figure 3A:
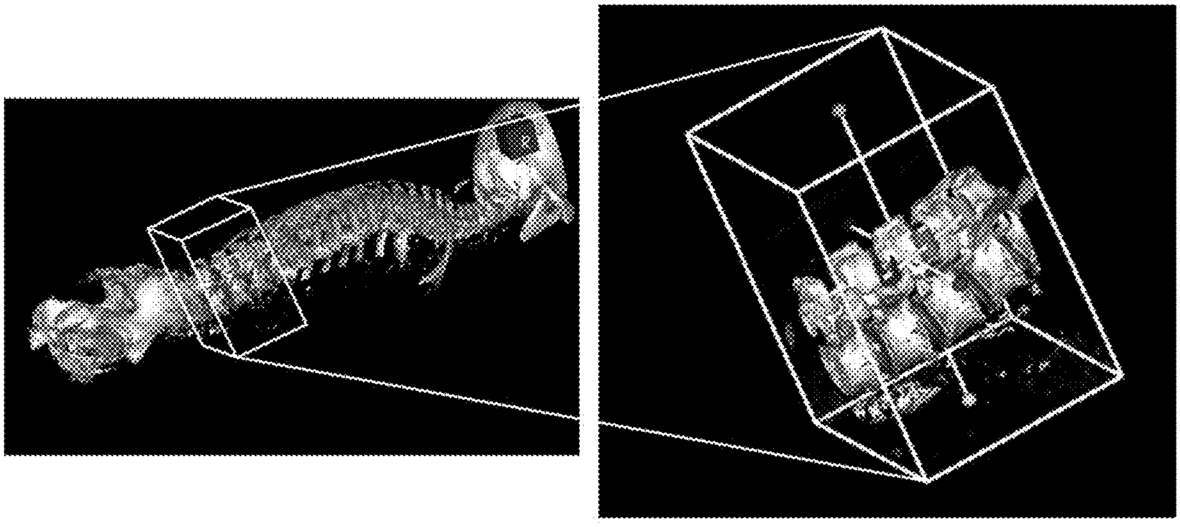
FIGS. 3A and 3B show examples for describing the process of making an operation plan on a CT image and extracting a volume of interest from the CT image.
Figure 3B:
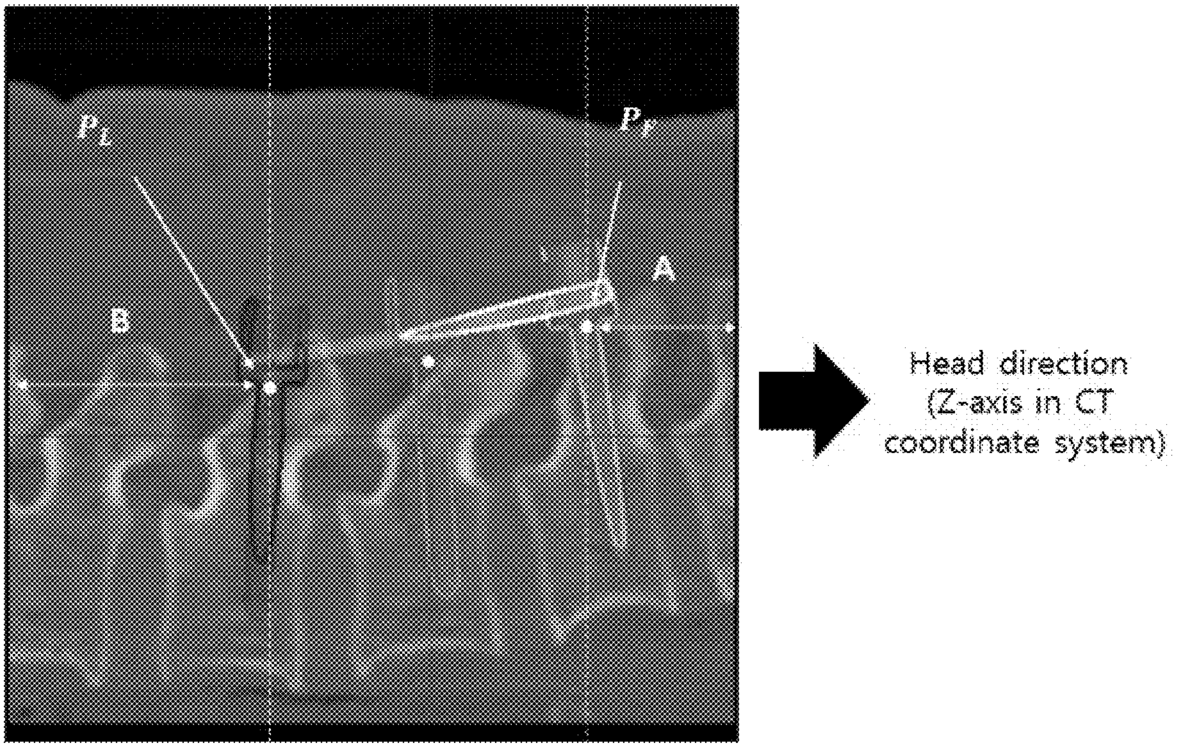

Referring to FIG. 3A, a doctor may set or adjust the volume of interest by controlling a white box provided on a left 3D image. Unlike FIG. 3A, referring to FIG. 3B, left and right margins (a, b) having default sizes with respect to, for example, the planning object, i.e., the screw are automatically extracted.

Figure 4:
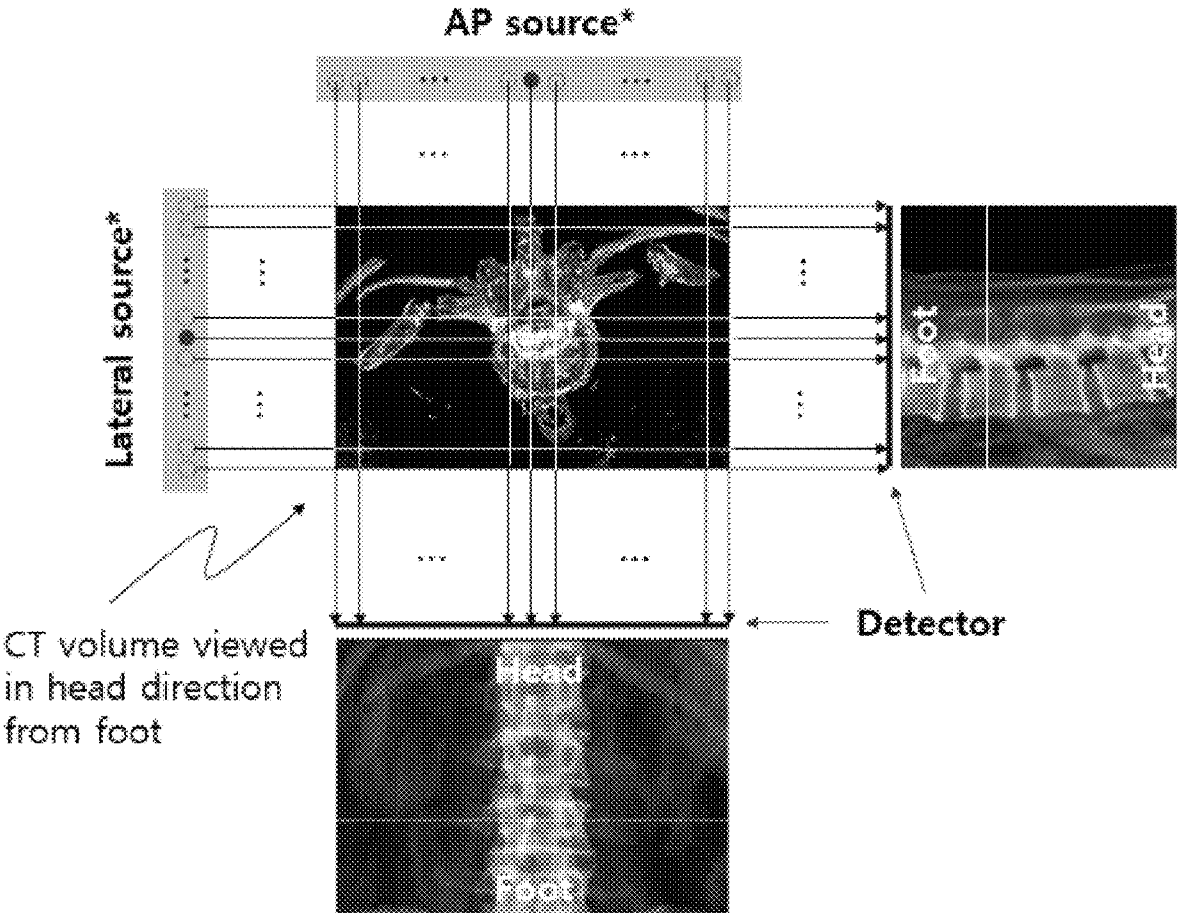
FIG. 4 shows an example for describing that a DRR image is generated from a CT image based on orthogonal projection.

From such extracted volume of interest, an anterior-posterior (AP) image and a lateral-lateral (LL) image are generated as digitally reconstructed radiograph (DRR) images (S4). In other words, as shown in FIG. 4, the AP image and the LL image are virtual C-arm images based on a CT coordinate system given by CT equipment, in which orthogonal projection is used to generate the AP image by an AP source and a detector and to generate the LL image by an LL source and a detector.

Next, the AP image and the LL image of the surgical site are acquired through the C-arm equipment during the operation (S5), and the C-arm equipment is registered to a spatial coordinate system based on a marker placed on a part of a patient's body (hereinafter, referred to as a 'PM' marker) or a marker to be referenced in other operative space (S6). Korean Patent No. KR2203544 filed by the present applicant's discloses technology of registering the C-arm equipment to a 3D space or registering a 2D image to the 3D space, and Patent 544' is incorporated by reference into the present disclosure in its entirety. The technology for registering the C-arm equipment to the space have been publicly known in many other documents in addition to Patent 544', and the disclosure is not limited to specific spatial registration technology.

Figure 5:
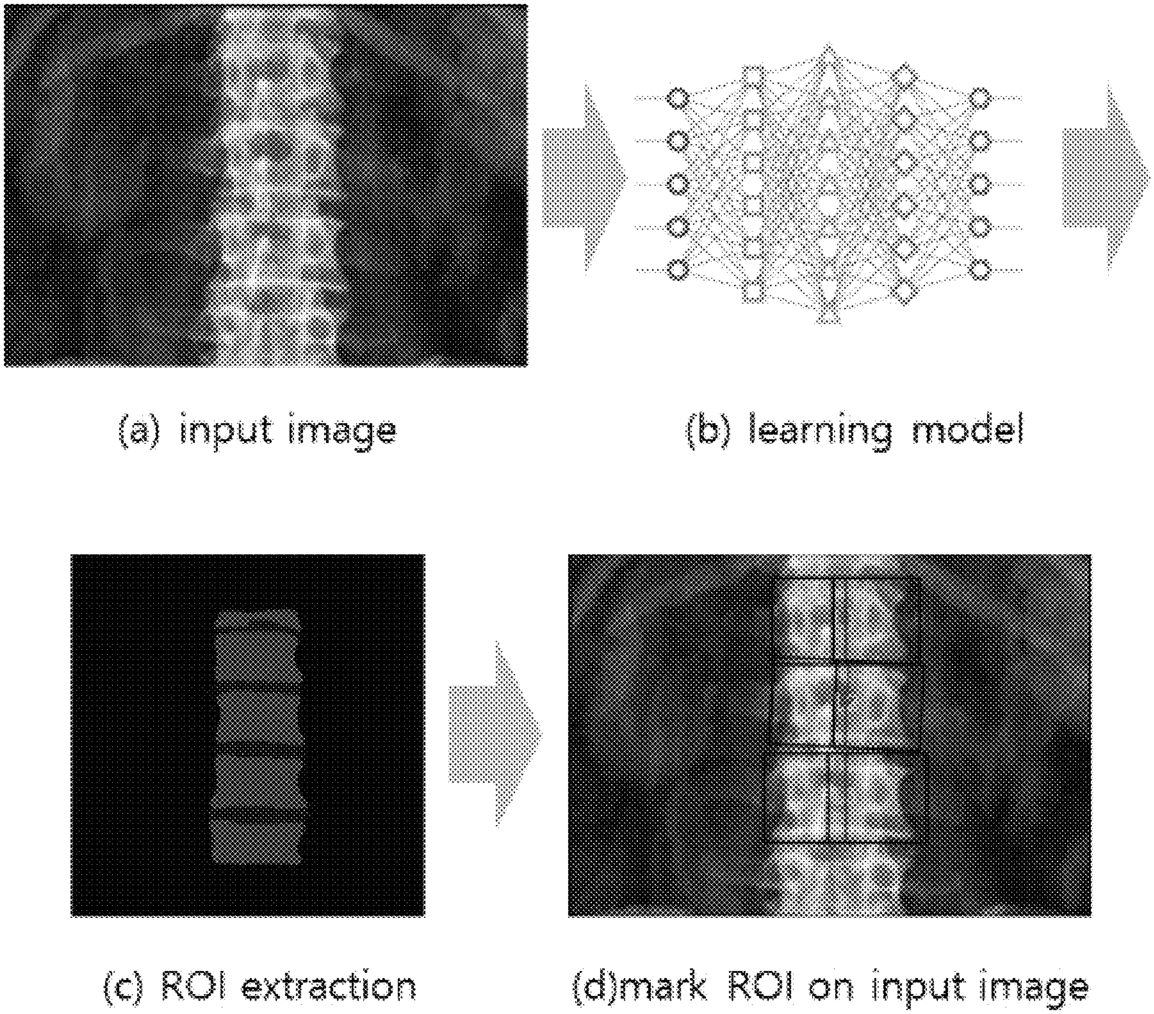
FIG. 5 shows an example for describing the process of automatically generating a region of interest after labeling through machine learning in an AP image.

The image registration apparatus 10 sets a first region of interest (ROI) and a second region of interest (ROI) for the DRR image and the C-arm image, respectively (S7 and S8). Each region of interest may be set in units of vertebral bones in the case of an operation of fixing a pedicle screw. As shown in FIG. 5, the region of interest may be extracted and labeled in units of vertebral bones through machine learning, and may be defined as a rectangle including each vertebral bone.

Figure 6A:
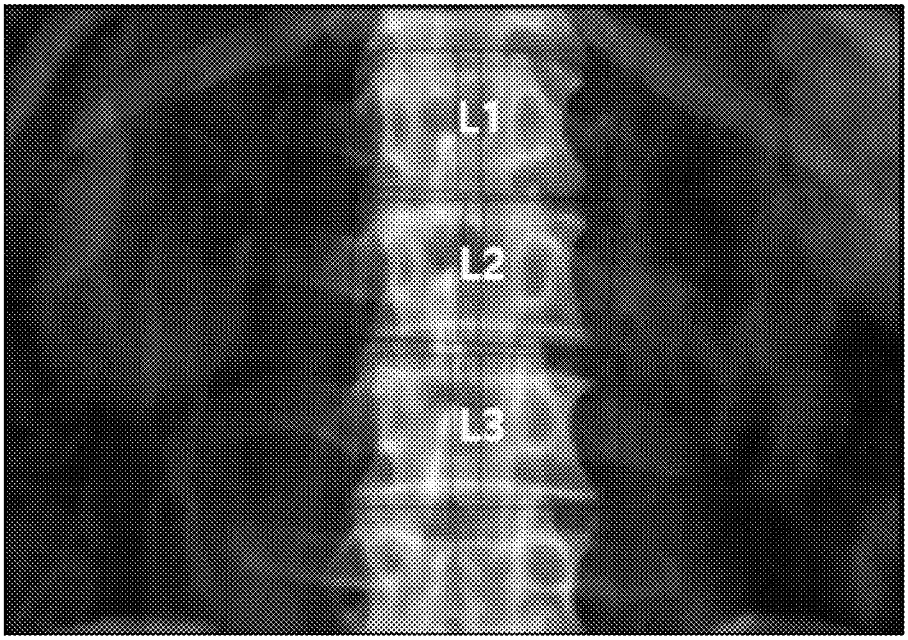
FIGS. 6A and 6B shows an example of the result of generating a first region of interest as the DRR image in an AP image and an LL image.
Figure 6B:
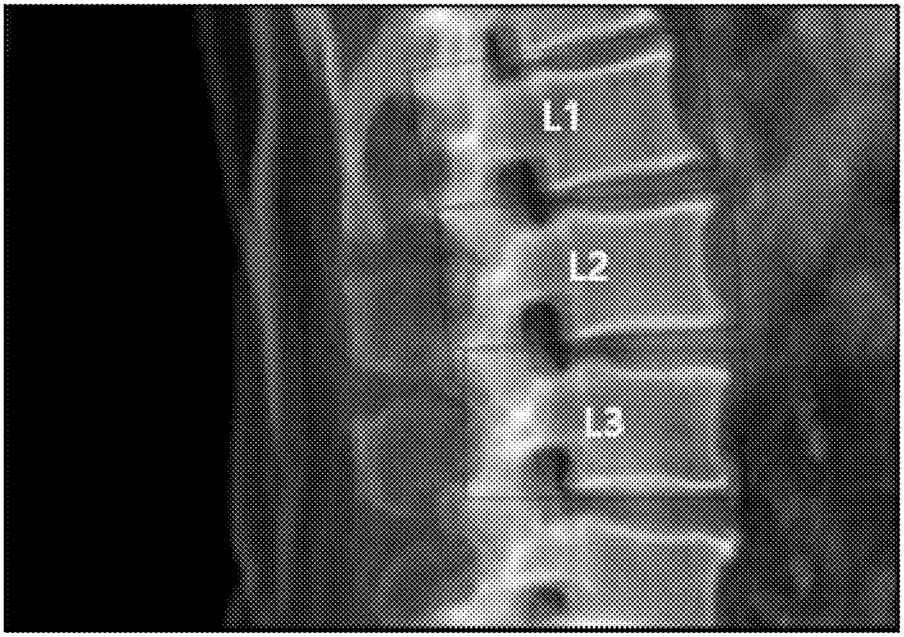
Figure 7A:
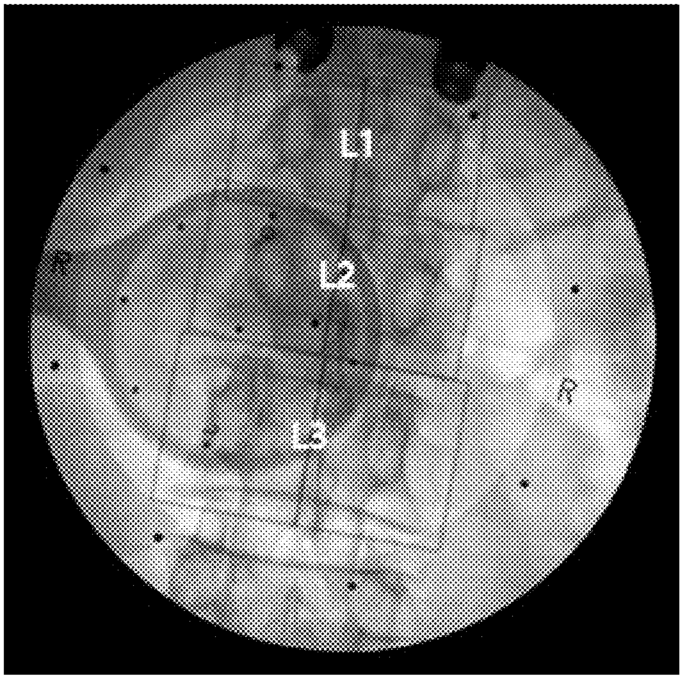
FIGS. 7A and 7B show an example of the result of generating a second region of interest as a C-arm image in the AP image and the LL image.
Figure 7B:
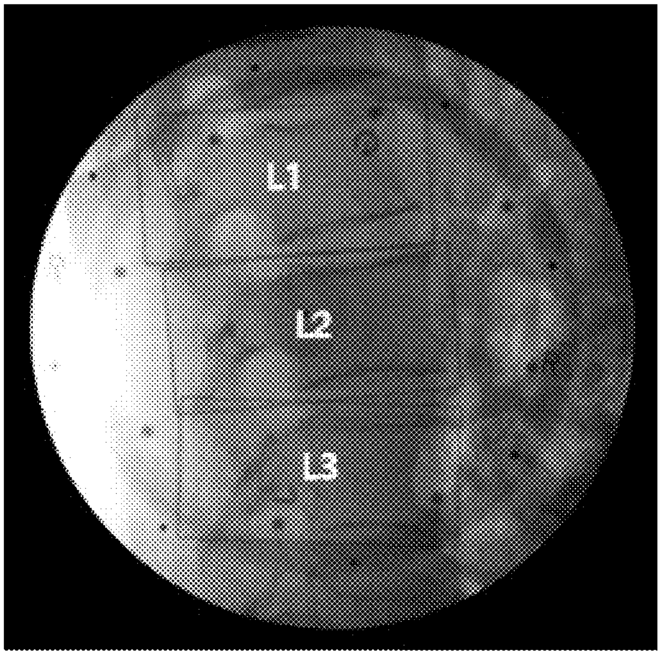

FIGS. 6A and 6B show the results of extracting the first region of interest in the AP image and the LL image of the labeled DRR image, and FIGS. 7A and 7B show the results of extracting the second region of interest in the AP image and the LL image of the labeled C-arm.

Here, it is noted that the first region of interest for the DRR image and the second region of interest for the C-arm image are extracted equivalently to each other. At least the vertices of the rectangle of the region of interest are selected as points having equivalences corresponding to each other. The equivalence does not mean a perfect match, but for example means that the first region of interest and the second region of interest are extracted or selected so that a relationship between the image feature of the vertebral bone and four vertices the selected region of interest is kept constant.

In this embodiment, for example, with respect to the vertebral bone, the first region of interest and the second region of interest are selected so that the tip of the spinous process can be disposed at the center of the region of interest for the AP image, and the outer margin of the vertebral bone can be uniformly applied to the first and second regions of interest in each of the AP/LL images.

Figure 8:
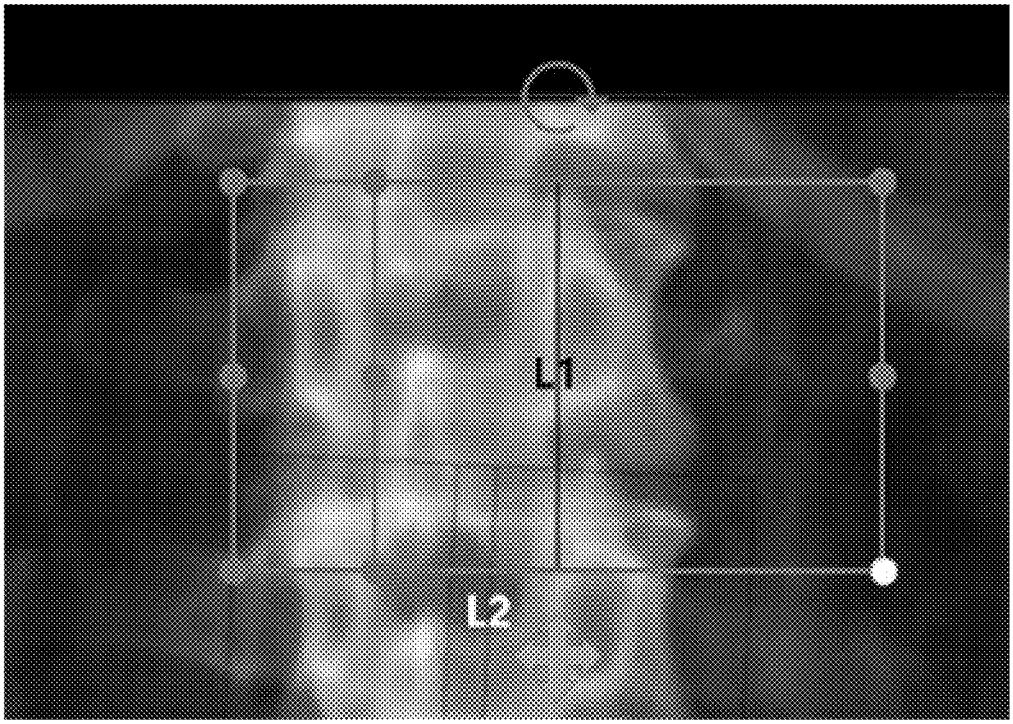
FIG. 8 shows an example of a user interface for resizing, positioning, rotating, setting SP, and the like for the region of interest.

Referring to FIG. 8, a doctor can resize, reposition, rotate, etc. the extracted region of interest through a given user interface, and can create a line pointing at a specific body part, e.g., the tip of the spinous process or adjust the region of interest to be aligned with a center line.

Next, the image registration apparatus 10 reconstructs the first region of interest displayed on the AP image and the LL image for the DRR image to a space, i.e., a volume of interest (S9). Intuitively, when the first region of interest in the AP image is moved parallel to a normal vector of the AP image on the assumption that the AP image is positioned at the virtual detector and at the same time the first region of interest in the LL image is moved parallel to the normal vector of the LL image on the assumption that the LL image is positioned at the virtual detector, a space where two planes intersect, i.e., a space where the first regions of interest on the two planes intersect each other will be called a first volume of interest.

The process of calculating the first volume of interest based on a coordinate system will be described with reference to FIGS. 9 to 13.

Referring to FIG. 9, a first vertex A1 of the first region of interest on the AP image and a virtual detector plane on which the AP image is positioned in the CT coordinate system are defined for the first region of interest with respect to the vertebral bone labeled with L3. Further, the virtual detector plane on which the LL image is positioned is defined, and the first region of interest on the LL image is also marked. Intuitively, when a volume formed by the intersection between the AP image and the LL image plane in a space is called the CT volume, the CT volume is expressed as a hexahedron that has six boundary faces and a three-axial CT coordinate system.

Because the DRR image is based on the orthogonal projection, such a hexahedral CT volume is formed, and the normal vector passing through $A_1$ reaches a certain height of $A'_1$ while intersecting the top and bottom boundary faces of the CT volume.

Therefore, $A'_1$ and the points $I_1$ and $I_2$ intersecting the top and bottom boundary faces are obtained as follows.

$$A'_1=\lambda_1 N_{AP}+A_1 \quad \text{[Equation 1]}$$

$$I_1=f_{inter}(\pi_{Top},A'_1,A_1) \quad \text{[Equation 2]}$$

$$I_2=f_{inter}(\pi_{Bot},A'_1,A_1) \quad \text{[Equation 3]}$$

Where, $\lambda_1$ is an arbitrary number, $N_{AP}$ is a normal vector to the AP plane, and $f_{inter}$ is a function that takes two points and one plane as input variables and obtains intersection points between a line connecting the two points and the plane.

Therefore, $I_1$ is obtained as follows.

$$I_1 = A_1 + \frac{N_{AP}^T(P_{Top} - A_1)}{N_{AP}^T(A'_1 - A_1)}(A'_1 - A_1) \quad \text{[Equation 4]}$$

Figure 9A:
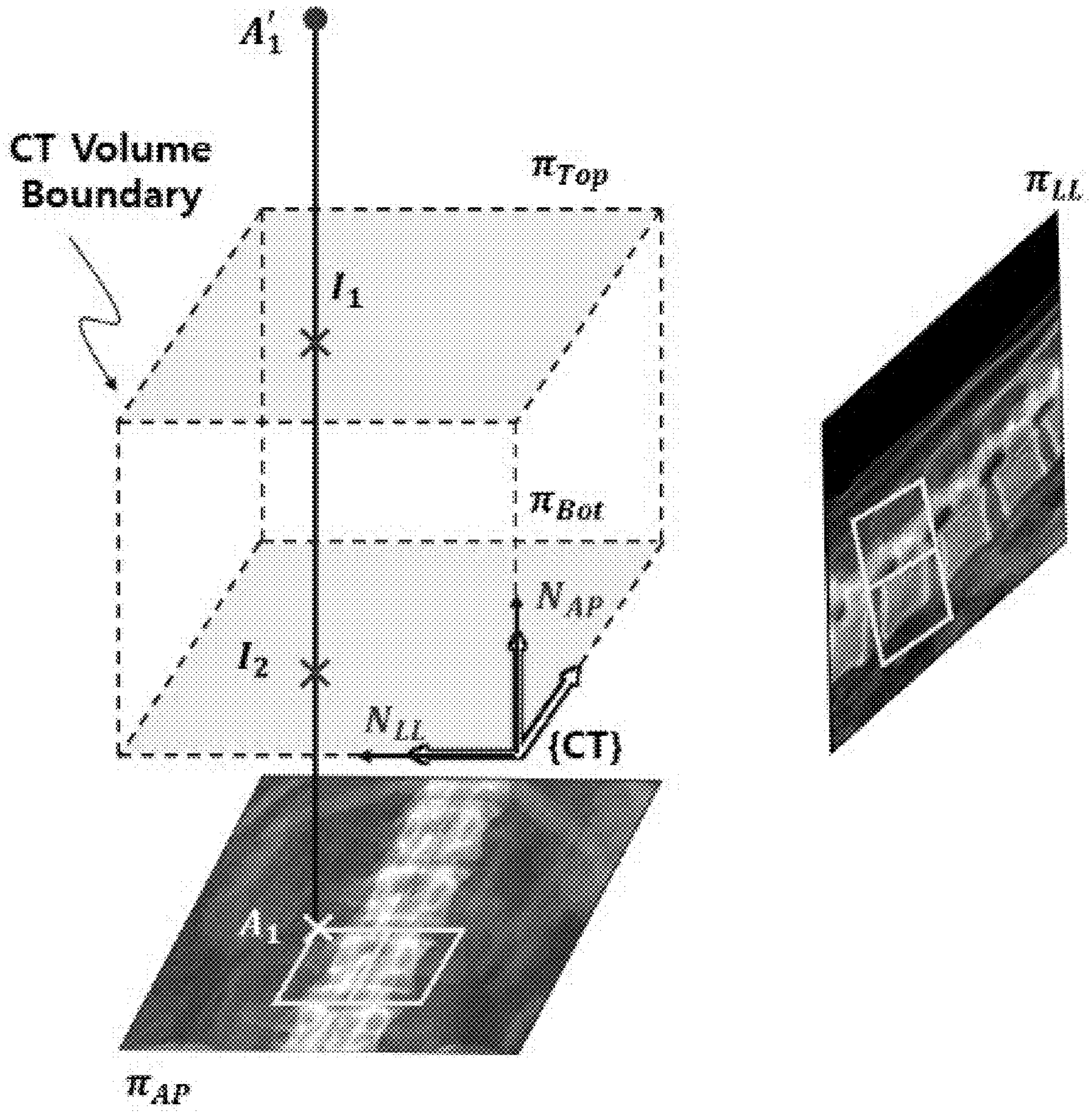
FIGS. 9A to 9D are views for describing a process of reconstructing vertices of a first region of interest in a CT volume.
Figure 9B:
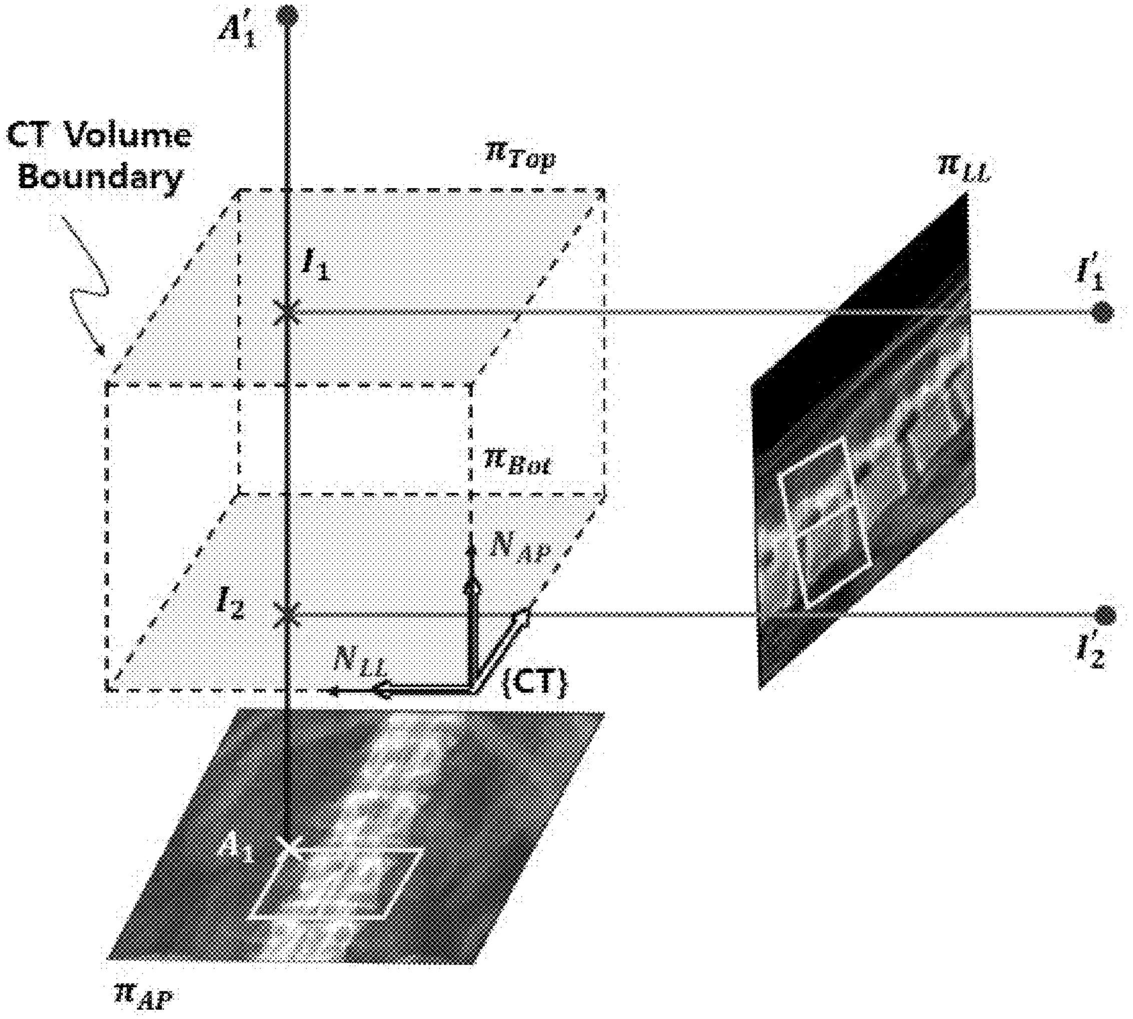

Where, $P_{Top}$ is $\pi_{Top}$, and $I_2$ is obtained in the same way as $I_1$. Referring to FIG. 9B, let $I'_1$ and $I'_2$ be arbitrary points on arbitrary normal starting from $I_1$ and $I_2$ and perpendicularly penetrating the LL image plane, respectively, $I'_1$ and $I'_2$ are expressed as follows.

$$I'_1=\lambda_2 N_{LL}+I_1 \quad \text{[Equation 5]}$$

$$I'_2=\lambda_2 N_{LL}+I_2 \quad \text{[Equation 6]}$$

Where, $\lambda_2$ is an arbitrary number, and $N_{LL}$ is a normal vector of the LL plane.

Figure 9C:
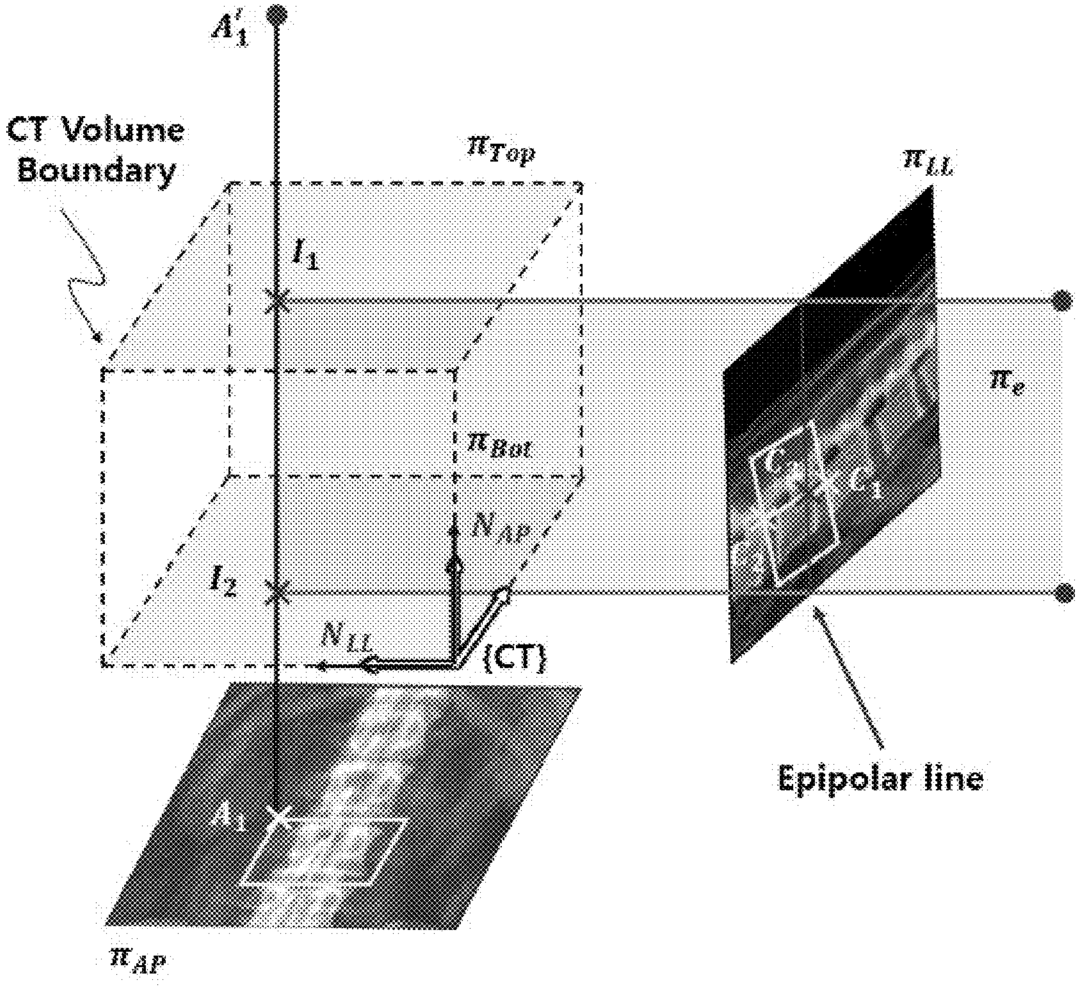

Next, referring to FIG. 9C, the epipolar line of the vertex $A_1$ is obtained by connecting intersection points between the LL image plane and line segments from $I_1$ and $I_2$ to $I'_1$ and $I'_2$. Further, intersection points between the epipolar line and any position in the region of interest on the LL image are obtained. In FIG. 9C, the intersection point $C_3$ between the epipolar line and a line segment connecting the centers $C_1$ and $C_2$ on the left and right sides in the first region of interest is obtained.

Figure 9D:
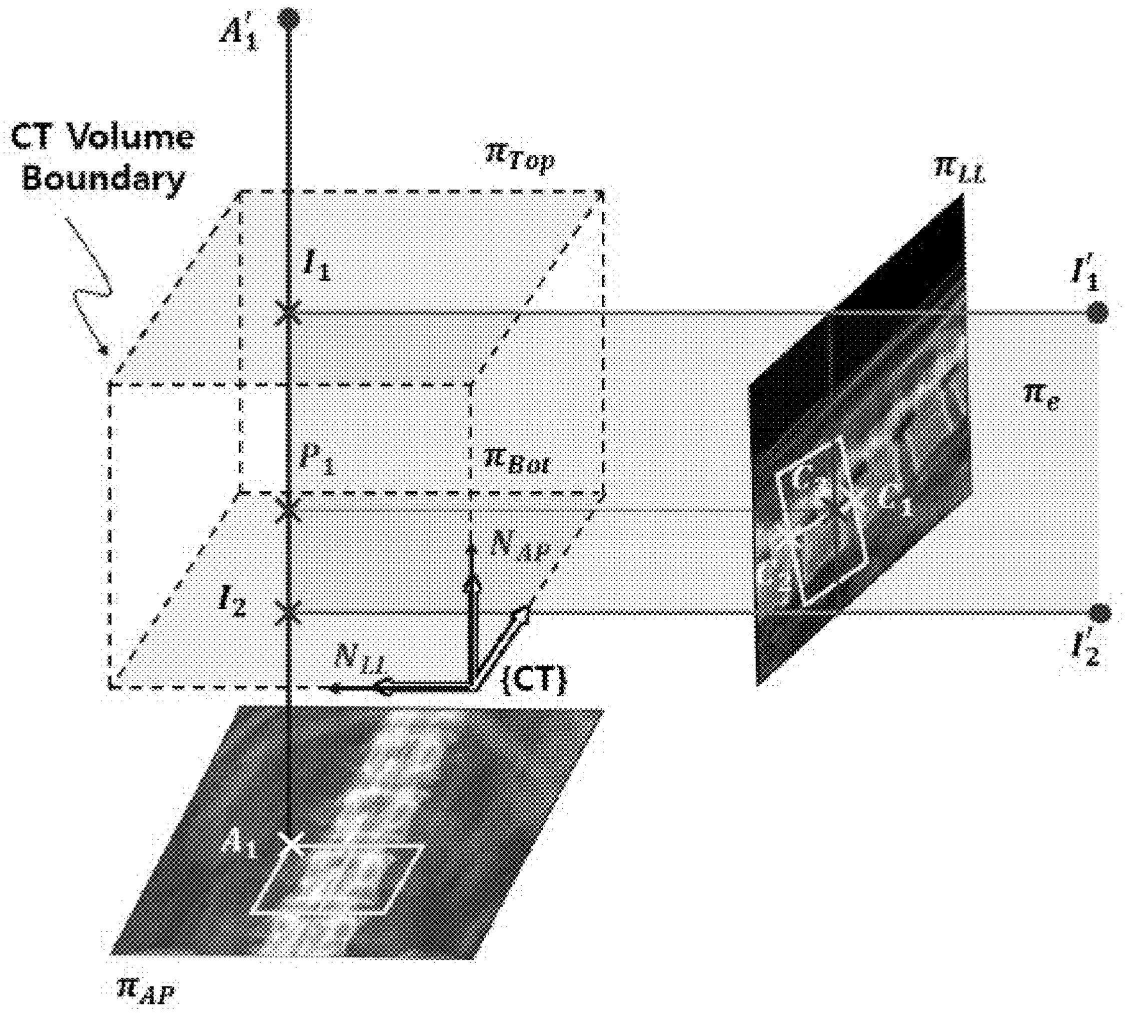

By projecting the intersection point $C_3$ between the region of interest and the epipolar line obtained as above onto the normal $A_1$-$A'_1$ from the vertex $A_1$, $P_1$ is obtained as shown in FIG. 9D. Here, if the position of the region of interest intersecting the epipolar line is taken as a top side, $P_1$ is positioned parallel to the top side of the first region of interest of the LL image. Therefore, it is noted that the point $P_1$ in the CT volume corresponding to $A_1$ is selectable on the normal from $A_1$ at any position within positions parallel to the top and bottom sides of the region of interest on the LL image.

By applying the same process as that of $A_1$ to the other three vertices, it will be understood that the plane of the first region of interest on the AP image is reconstructed as transferred to the CT volume. Likewise, it will be understood that the vertices on the LL image are reconstructed as transferred to the CT volume.

Figure 10:
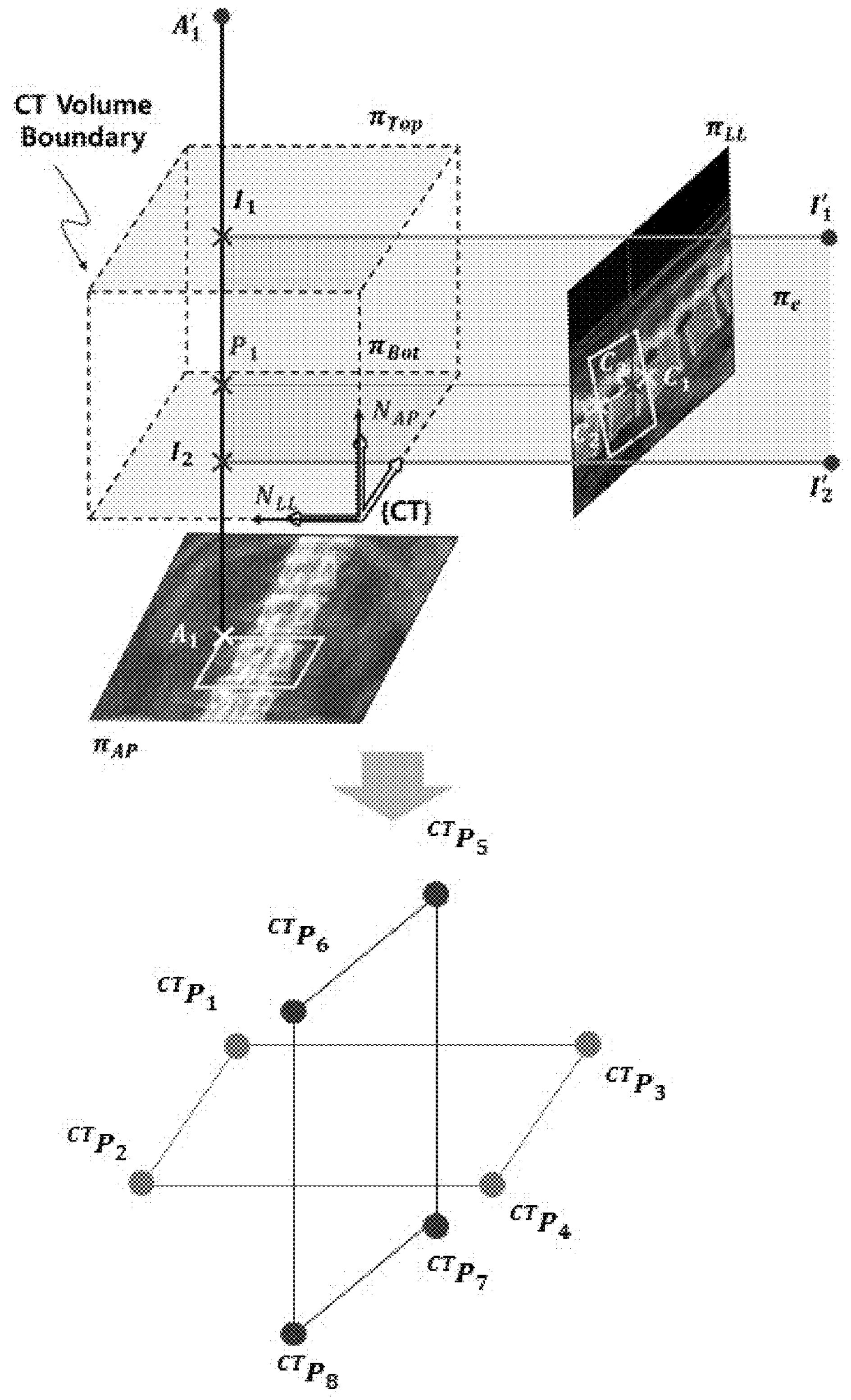
FIG. 10 shows an example to describe the result of reconstructing eight vertices of a first region of interest in a CT volume.

FIG. 10 shows an example that eight vertices $A_1$ to $A_8$ defining the first region of interest are reconstructed as eight points ${}^{CT}P_1$, ${}^{CT}P_2$, . . . ${}^{CT}P_8$ within the CT volume.

Figure 11:
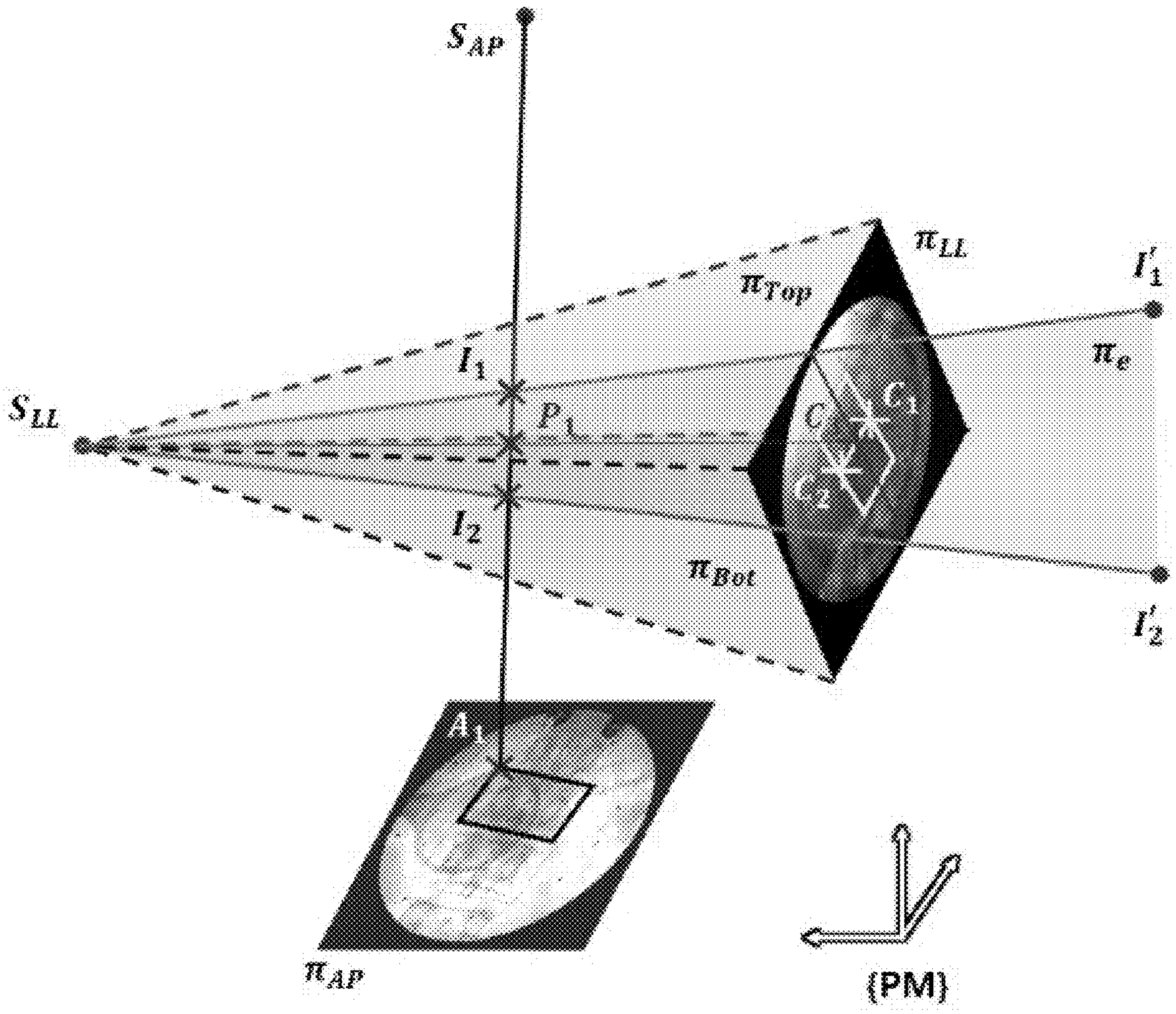
FIG. 11 is a view for describing a process of reconstructing vertices of a second region of interest in a C-arm volume.

FIG. 11 shows a relationship in which one vertex $A_1$ defining the second region of interest on the C-arm image is reconstructed to the C-arm volume.

Compared to FIGS. 9A to 9D, the C-arm image is obtained based on perspective projection, and thus a vector between the source and the detector is defined as a direction vector based on a PM coordinate system using the PM marker instead of using the unit vectors on the orthogonal CT coordinate system.

Therefore, $I_1$, $I_2$, $I'_1$, $I'_2$, $C_3$, and $P_1$ in FIG. 11 are obtained as follows.

$$I_1 = f_{inter}(\pi_{Top}, S_{AP}, A_1) \quad \text{[Equation 7]}$$

$$I_2 = f_{inter}(\pi_{Bot}, S_{AP}, A_1) \quad \text{[Equation 8]}$$

$$I'_1 = \lambda_2 \frac{I_1 - S_{LL}}{\|I_1 - S_{LL}\|} + S_{LL} \quad \text{[Equation 9]}$$

$$I'_2 = \lambda_2 \frac{I_2 - S_{LL}}{\|I_2 - S_{LL}\|} + S_{LL} \quad \text{[Equation 10]}$$

$$C_3 = f_{inter}(\pi_e, C_1, C_2) \quad \text{[Equation 11]}$$

$$P_1 = \{(I_1 - C_3)^T N\}N + C_3 \quad \text{[Equation 12]}$$

Where, $S_{LL}$ is a source position on the LL image, $\lambda_2$ is an arbitrary number, $$N = \frac{C_3 - S_{LL}}{\|C_3 - S_{LL}\|},$$

and $C_1$ and $C_2$ are the centers of the left and right sides in the region of interest on the LL image.

By repeating the same process with respect to eight vertices $A_1$ to $A_8$, eight points ${}^{PM}P_1$, ${}^{PM}P_2$, . . . ${}^{PM}P_8$ are reconstructed in the C-arm volume as shown in FIG. 12.

Figure 12:
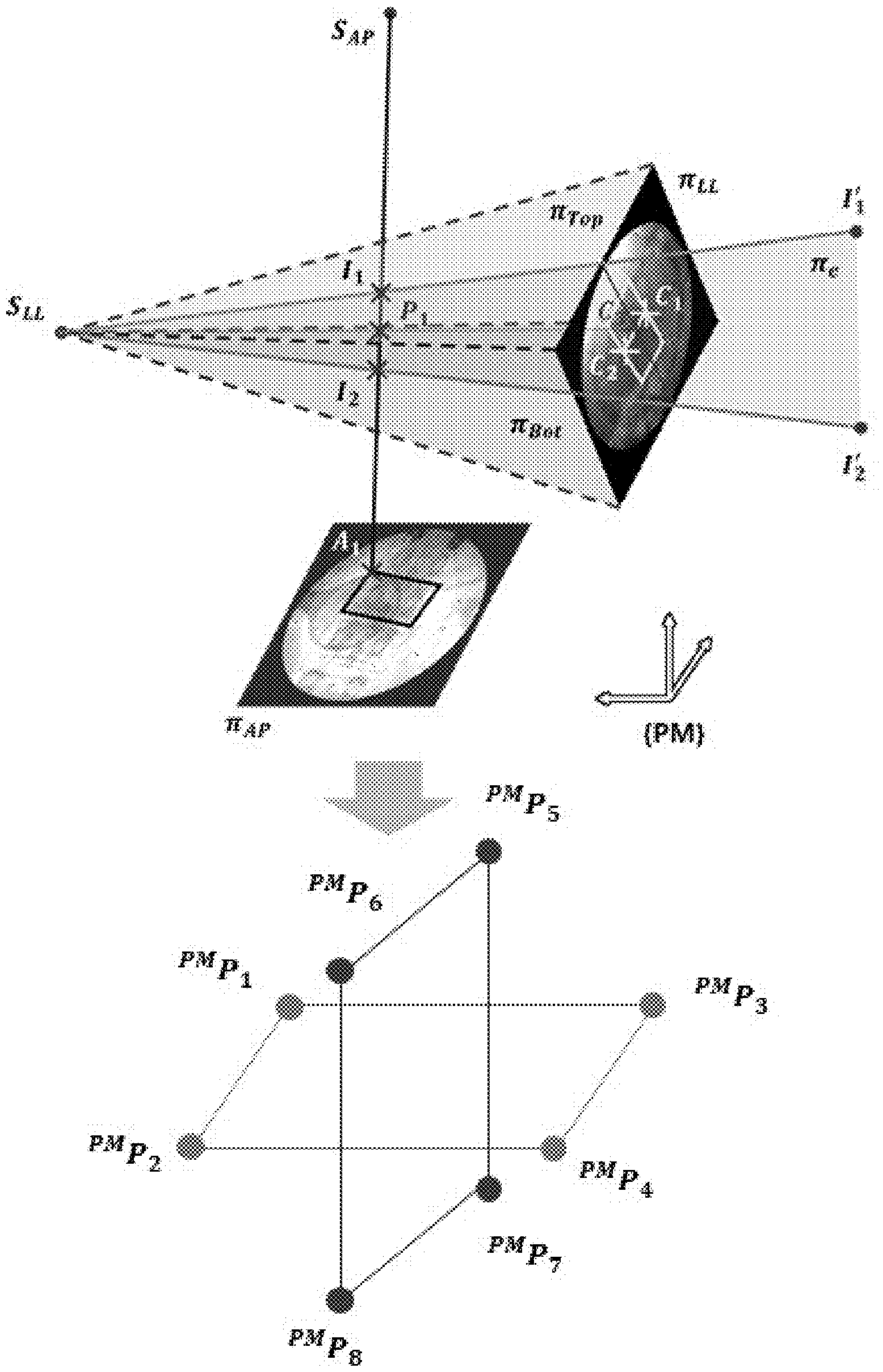
FIG. 12 is a view for describing the result of reconstructing eight vertices of a second region of interest in a C-arm volume.

Referring to FIGS. 10 and 12, eight points reconstructed in the CT volume and eight points reconstructed in the C-arm volume look as if the region of interest on the AP image and the region of interest on the LL image intersect at their centers. It will be understood that these eight points serve as the midlines of a hexahedron while forming a volume of interest.

Referring back to the flowchart of FIG. 2, the image registration apparatus 10 reconstructs the eight points or the first and second volumes of interest in the CT volume and the C-arm volume, respectively, and calculates a rotation angle between the reference position of a patient's surgical site and the corresponding reference position with respect to a predetermined axis (S10).

In this embodiment, the reference position is the tip of the spinous process, and the corresponding first reference position corresponds to the normal vector of an AXIAL image defined in the same direction as the vector of the cross product between the normal vector of the AP image plane and the normal vector of the LL image plane. However, a first origin determining the position of the rotation axis ideally reflects the rotation center of the spine, but it is difficult to define this. Therefore, one of two options (to be described later) is selected.

Figure 13A:
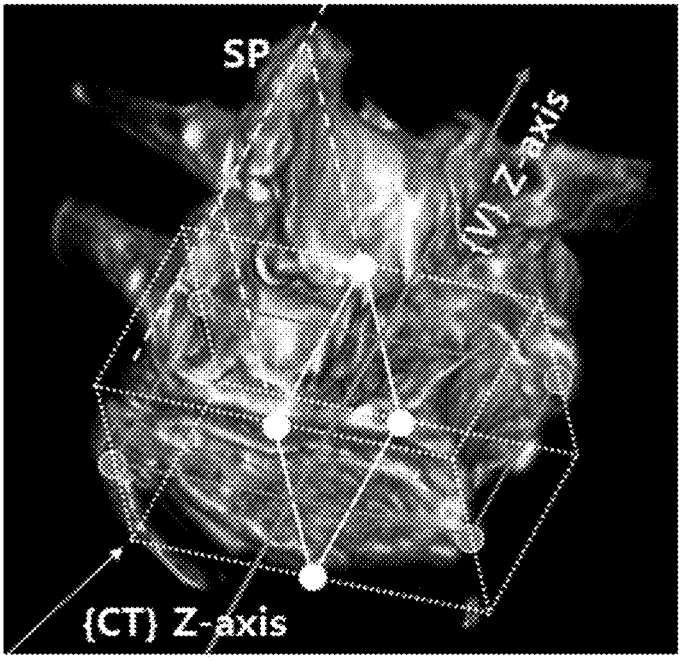
FIGS. 13A and 13B are views for describing a case where an axial direction of a first volume of interest and a tip line of a spinous process are aligned and a caser where they are misaligned and rotated.

First, referring to FIG. 13A, it will be understood that there is no rotation in this case because the end of the spinous process SP and a line segment between ${}^{CT}P_5$ and ${}^{CT}P_6$ shown in FIG. 10 are different only in height and have no lateral deviation.

Figure 13B:
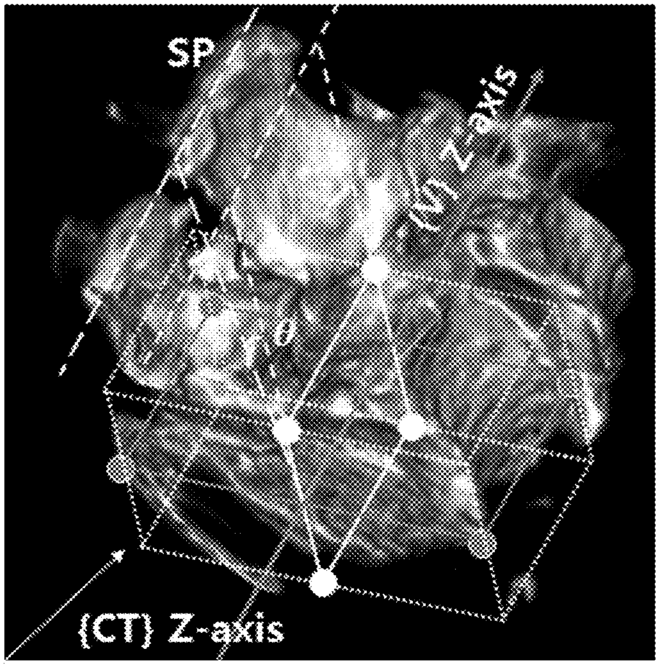

On the other hand, referring to FIG. 13B, it will be understood that the axis passing through the center of the first volume of interest is tilted by an angle of θ because there is lateral deviation between the end of the spinous process SP and the line segment between ${}^{CT}P_5$ and ${}^{CT}P_6$.

Figure 14:
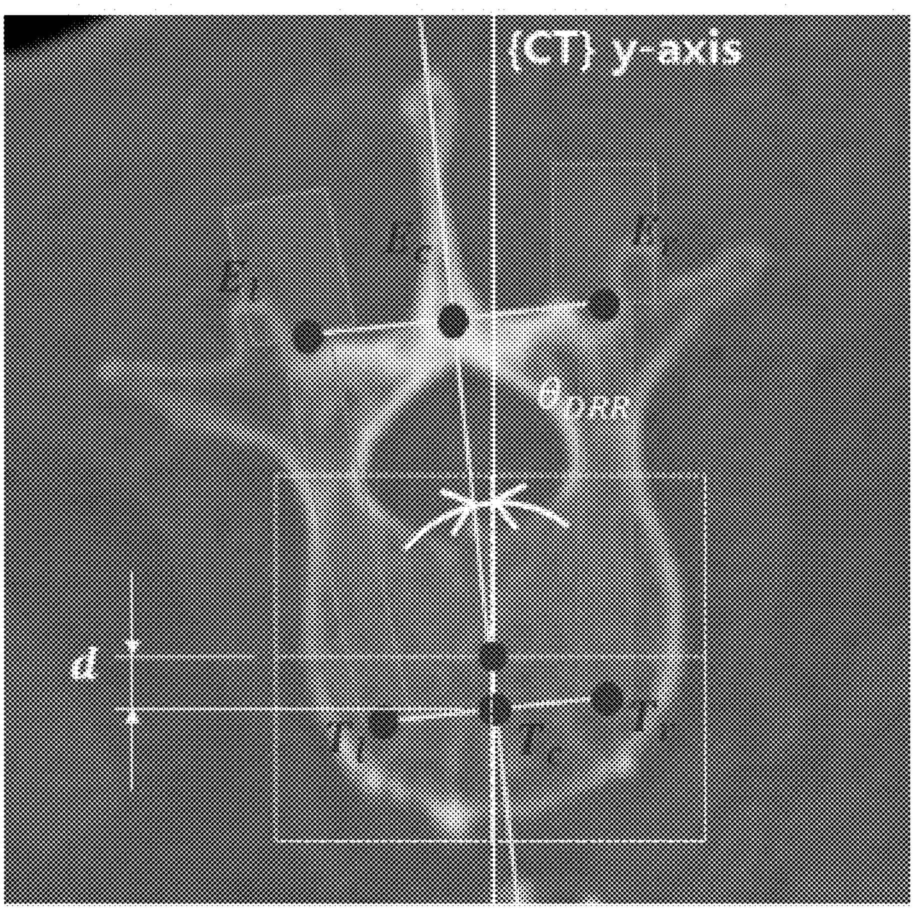
FIG. 14 shows an example for describing a method of determining a first rotation angle based on a planning object position of which an operation plan is made before an operation.

To obtain the tilted rotation angle θ (hereinafter referred to as a 'first rotation angle'), a doctor may use a pre-operative planning object as shown in FIG. 14. Referring to FIG. 14, an angle between a line $E_c$-$T_c$ that connects the center $E_c$ between the entry points $E_r$ and $E_l$ at which a pair of screws enter the left and right pedicles with respect to the axis and the center $T_c$ between the positions $T_l$ and $T_r$ (hereinafter referred to as 'targets') to which the distal ends of the screws are finally mounted, and a longitudinal line segment that passes through the center of the axial plane of the first volume of interest, i.e., the line segment between ${}^{PT}P_6$ and ${}^{PT}P_8$ is obtained as a first rotation angle $\theta_{DRR}$.

In this case, it will be understood that the first origin through which the first rotation axis passes is selected as the center T c between the left and right targets $T_l$ and $T_r$, and different in height by 'd' from the center of the first volume of interest. This makes it easy to calculate a rotation value based on a doctor's operation plan, and helps to perform quick registration processing. As discussed for the rotation of the C-arm image, the center of the first volume of interest may be used instead of the target center as the first rotation origin.

Figure 15:
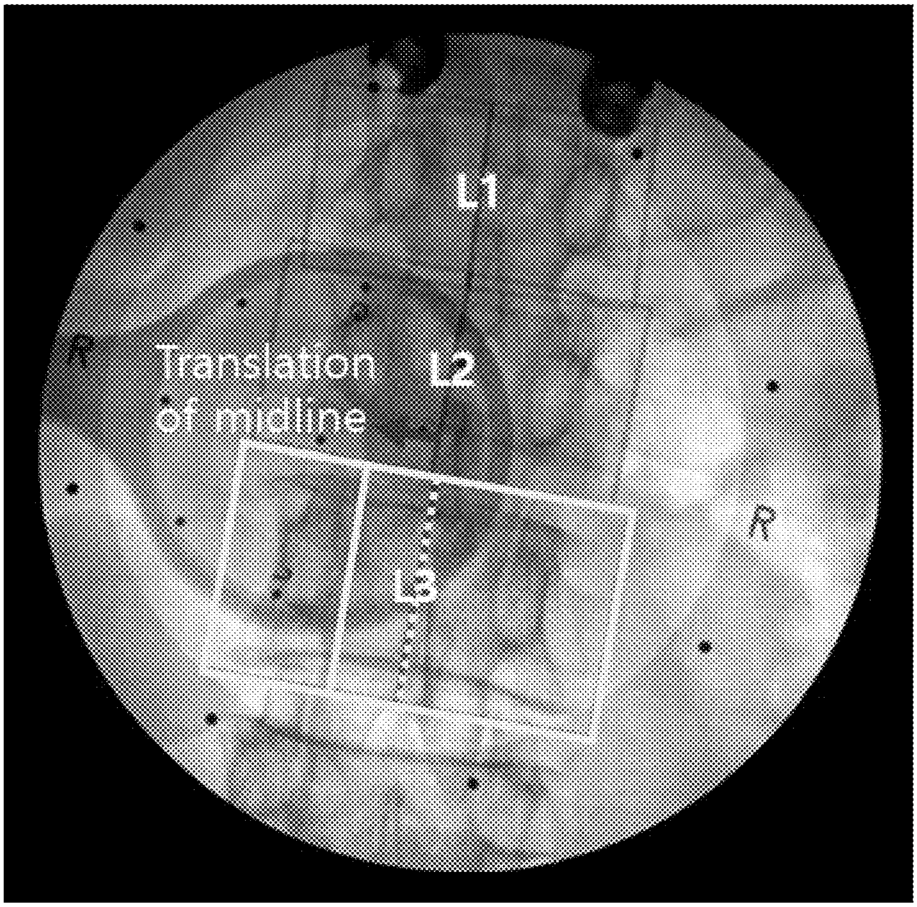
FIG. 15 shows an example for describing a user interface through which a user sets a tip line of a spinous process in a C-arm AP image.

Meanwhile, as shown in FIG. 15, it is possible to acquire the true AP and LL images of the C-arm image. Therefore, a user interface may be provided so that a doctor can move the center line of the second region of interest on the AP image to match the tip of the spinous process in order to set the tip of the spinous process in person in this stage even though the center of the second region of interest on the AP image often matches the tip of the spinous process. This may also be applied to the DRR image.

Figure 16:
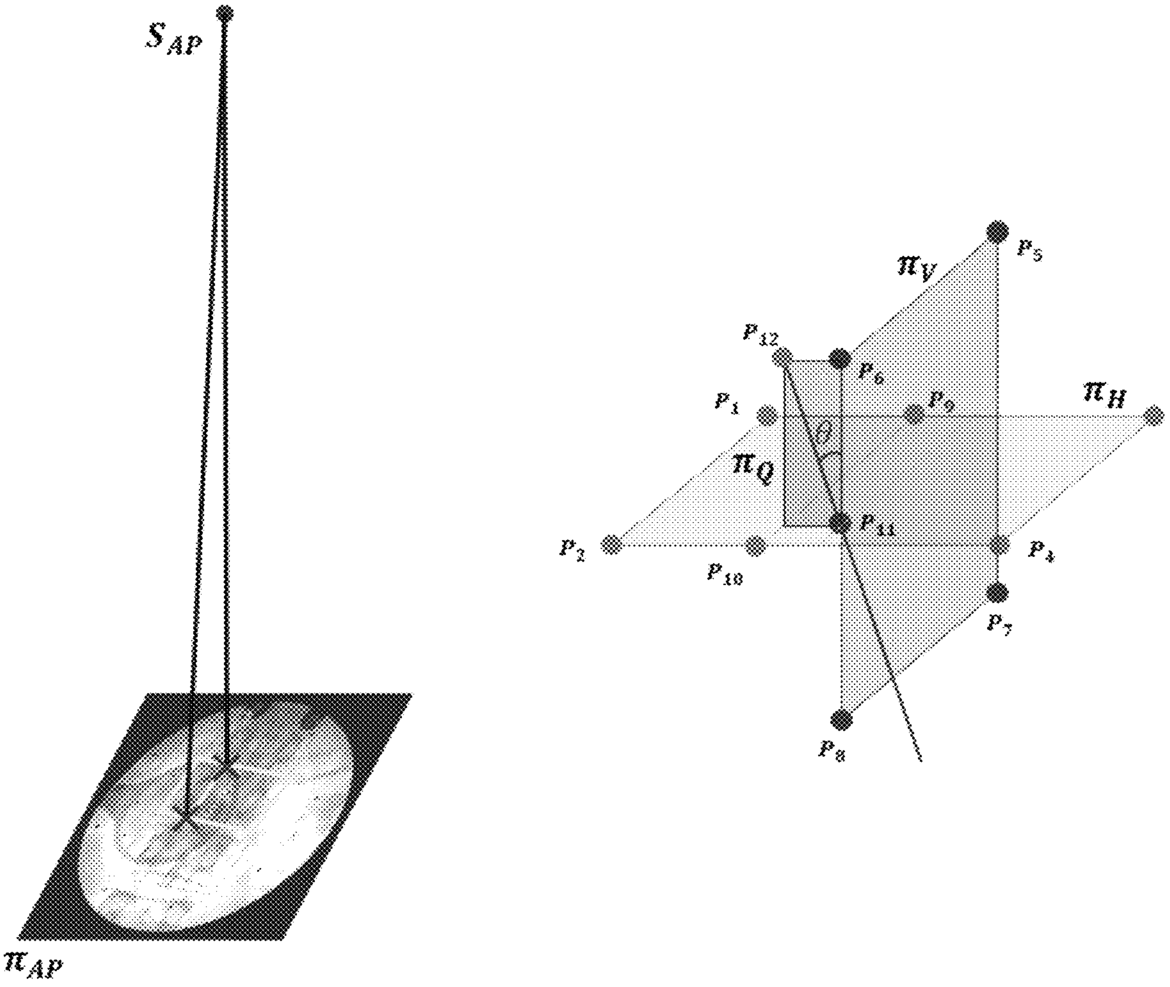
FIG. 16 shows an example for describing a process of calculating a second rotation angle based on a C-arm AP image.

As shown in FIG. 16, when the tip of the spinous process set by a user passes through $P_{12}$ and is parallel to $P_5$-$P_6$, a second rotation angle of the C-arm image may be obtained as an angle between a line $P_9$-$P_{10}$ of an input end spinous process tip projected at a height of $P_6$ and a line segment $P_5$-$P_6$ with respect to an intersection line between the plane formed by $P_1$ to $P_4$ and the plane formed by $P_5$ to $P_8$.

$$P_{11} = f_{inter}(\pi_H, P_6, P_8) \quad \text{[Equation 13]}$$

$$N = \frac{P_2 - P_4}{\|P_2 - P_4\|} \quad \text{[Equation 14]}$$

$$P_{12} = \{(P_{10} - P_{11})^T N\}N + P_6 \quad \text{[Equation 15]}$$

$$\theta_{C\text{-}arm} = a\cos\left(\left(\frac{P_{12} - P_{11}}{\|P_{12} - P_{11}\|}\right)^T \left(\frac{P_6 - P_{11}}{\|P_6 - P_{11}\|}\right)\right) \quad \text{[Equation 16]}$$

Where, $P_1$ to $P_8$ are points to which eight vertices of the second region of interest are reconstructed, and $P_9$ and $P_{10}$ are a spinous process tip line designated by a user.

It is noted that FIG. 16 illustrates a case where a horizontal plane formed by $P_1$ to $P_4$ and a vertical plane formed by $P_5$ to $P_8$ do not intersect except an intersection line.

Figure 17:
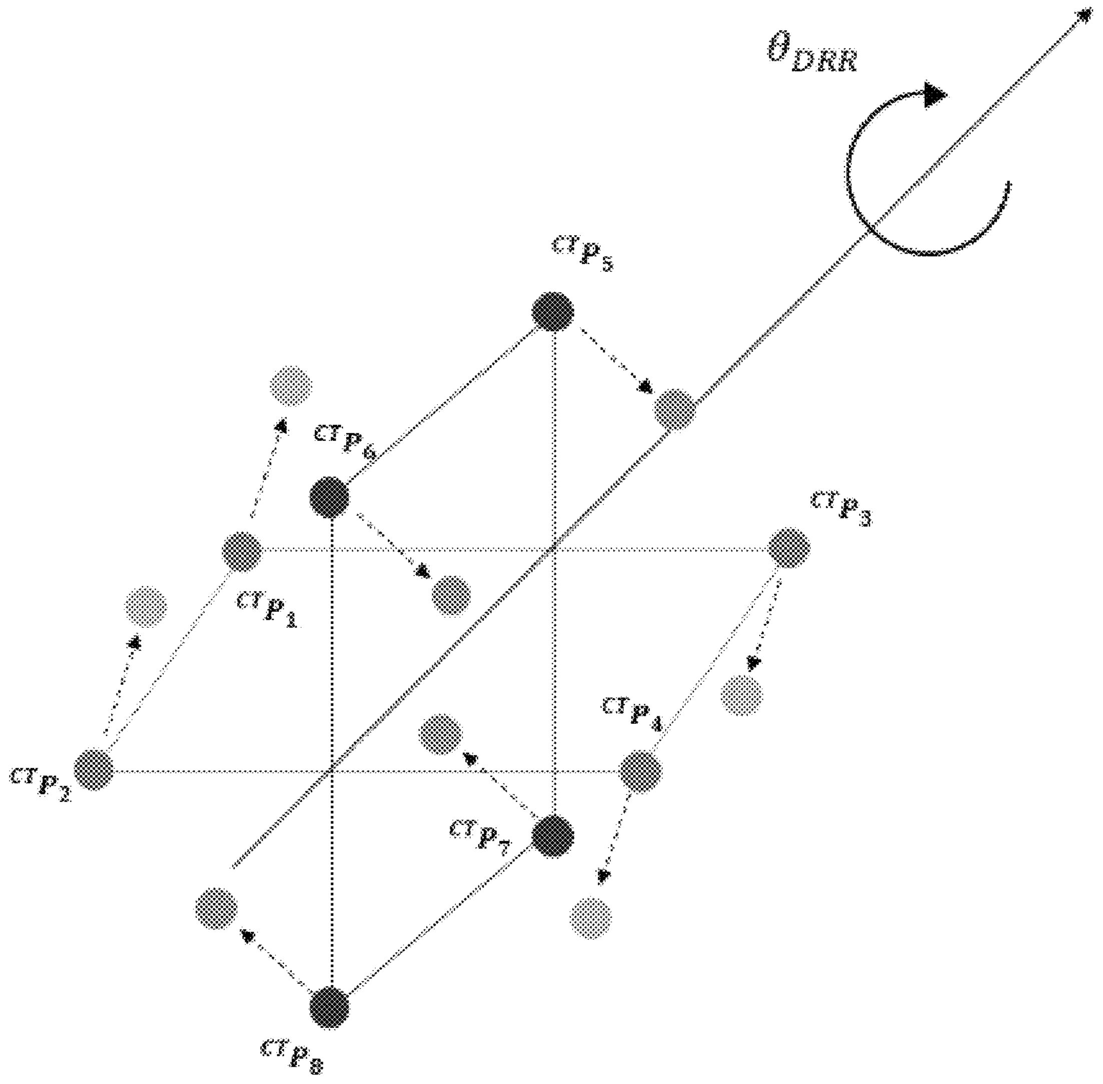
FIG. 17 shows a relationship between eight points reconstructed in a CT volume and points rotated by a first rotation angle.

FIG. 17 shows a relationship between eight points ${}^{CT}P_1$ to ${}^{CT}P_8$ reconstructed in the CT volume and points ${}^{CT}P'_1$ to ${}^{CT}P'_8$ rotated from the points ${}^{CT}P_1$ to ${}^{CT}P_8$ by the first rotation angle $\theta_{DRR}$ calculated with reference to FIG. 14. This shows the positions of the points reflecting the rotation of the spine with respect to the tip of the spinous process after reconstructing the first region of interest in the CT coordinate system to the CT volume. Similarly, for the second region of interest on the C-arm image, the point positions ${}^{PM}P'_1$ to ${}^{PM}P'_8$ calculated reflecting the rotation of a patient's spine during the operation may be obtained in the same way.

When a transformation relationship between the PM coordinate system and the CT coordinate system is applied to the rotated points, i.e., ${}^{PM}P'_1$ to ${}^{PM}P'_8$ and ${}^{CT}P'_1$ to ${}^{CT}P'_8$, the Euclidean distance therebetween should be 0 ideally. The optimal registration may be performed under the condition that the sum or average of the Euclidean distances between the eight point pairs is the smallest, and the purpose of initial registration is to obtain a transform matrix satisfying this condition (S11).

$$T_{PM}^{CT} \leftarrow \min_{T_{PM}^{CT}} \sum_{i=1}^{N} \|{}^{CT}P'_i - T_{PM}^{CT}\,{}^{PM}P'_i\|^2 \quad \text{[Equation 17]}$$

Where, $$T_{PM}^{CT}$$

is a transformation matrix from the PM coordinate system to the CT coordinate system.

Figure 18:
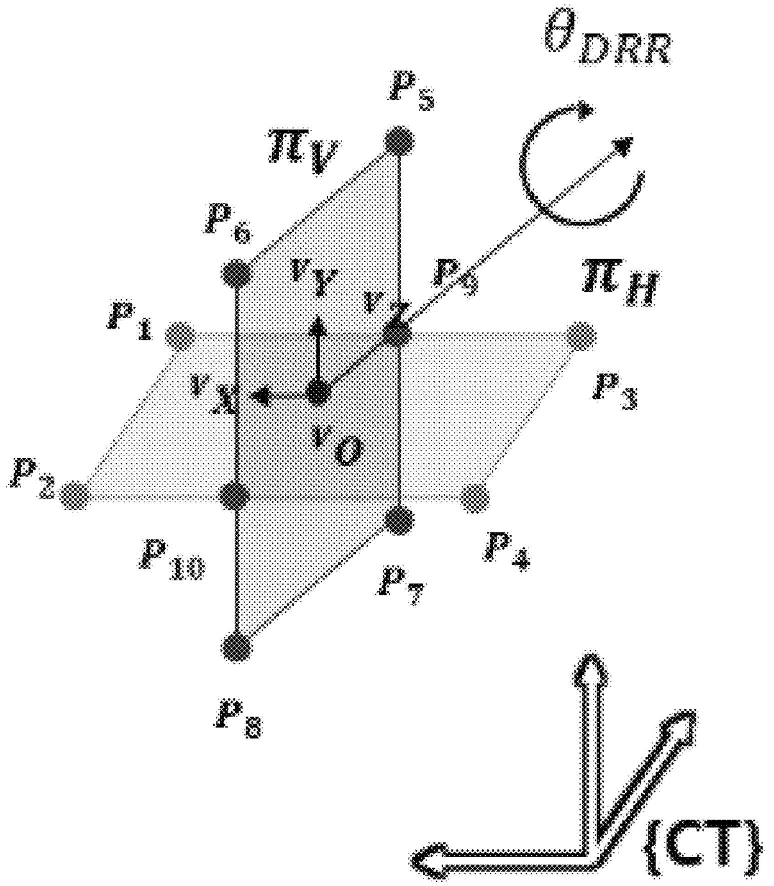
FIG. 18 is a view for describing a local coordinate system V, the origin of which is the center of a first volume of interest.

Referring to FIG. 18, a transformation relationship from the CT coordinate system to a V-local coordinate system will be described. Here, the origin of the V-local coordinate system is defined as follows based on the midpoint of the intersection line between the horizontal plane and the vertical plane.

$${}^{V}O = \frac{P_9 + P_{10}}{2} \quad \text{[Equation 18]}$$

Where, $P_9 = f_{inter}(\pi_V, P_1, P_3)$ $P_{10} = f_{inter}(\pi_V, P_2, P_4)$.

Thus, three axes ${}^{V}X$, ${}^{V}Y$, and ${}^{V}Z$ of the V-local coordinate system are defined as follows.

$${}^{V}X' = \frac{P_2 - P_4}{\|P_2 - P_4\|} \quad \text{[Equation 19]}$$

$${}^{V}Z = \frac{P_9 - P_{10}}{\|P_9 - P_{10}\|} \quad \text{[Equation 20]}$$

$${}^{V}Y = {}^{V}Z \times {}^{V}X' \quad \text{[Equation 21]}$$

$${}^{V}X = {}^{V}Y \times {}^{V}Z \quad \text{[Equation 22]}$$

In the V-local coordinate system, the position ${}^{V}P_i$ of $P_i$ is defined as follows.

$${}^{V}P_i = R_{CT}^{V}\,{}^{CT}P_i + t_{CT}^{V} \quad \text{[Equation 23]}$$

Where, $$R_{CT}^{V}$$

is a rotational transformation matrix from the CT coordinate system to the V-local coordinate system, and $$t_{CT}^{V}$$

is a translation vector between the CT coordinate system and the V-local coordinate system.

In addition, the points in the rotated V-local coordinate system are obtained as follows.

$${}^{V}P'_{i}=\text{Rodrigues}({}^{V}Z,\theta_{DRR}){}^{V}P_{i} \qquad \text{[Equation 24]}$$

Where, the Rodrigues function is defined as a function that rotates an object by an input rotation angle with respect to the input rotation axis.

Thus, the rotated point ${}^{CT}P'_{I}$ in the CT coordinate system is defined as follows.

$${}^{CT}P'_{i}=\left(R_{CT}^{V}\right)^{-1}{}^{V}P'_{i}-\left(R_{CT}^{V}\right)^{-1}t_{CT}^{V} \qquad \text{[Equation 25]}$$

Thus, the foregoing processes are applied to the eight points, and ${}^{PM}P'_{i}$ rotated from ${}^{PM}P_{i}$ in the PM coordinate system is calculated and input to the following equation.

$$T_{PM}^{CT}\leftarrow\min_{T_{PM}^{CT}}\sum_{i=1}^{N}\left\|{}^{CT}P'_{i}-T_{PM}^{CT}\,{}^{PM}P'_{i}\right\|^{2} \qquad \text{[Equation 26]}$$

When the initial registration is completed by finding the optimal transformation matrix, the image registration apparatus 10 derives the optimal transformation matrix while adjusting a search range of the DRR image and performs a registration optimization process, thereby completing the image registration (S12). The optimization process is publicly known based on global search, and thus detailed descriptions thereof will be omitted.

As described above, the image registration method has the advantage of increasing the accuracy of the image registration according to the rotation of a human body, and quickly performing the image registration processing.

The disclosure may be implemented as a computer program recording medium in which a computer program is recorded to perform the image registration method on a computer.

Further, the disclosure may also be implemented by the medical operating robot system based on the foregoing image registration method.

Figure 19:
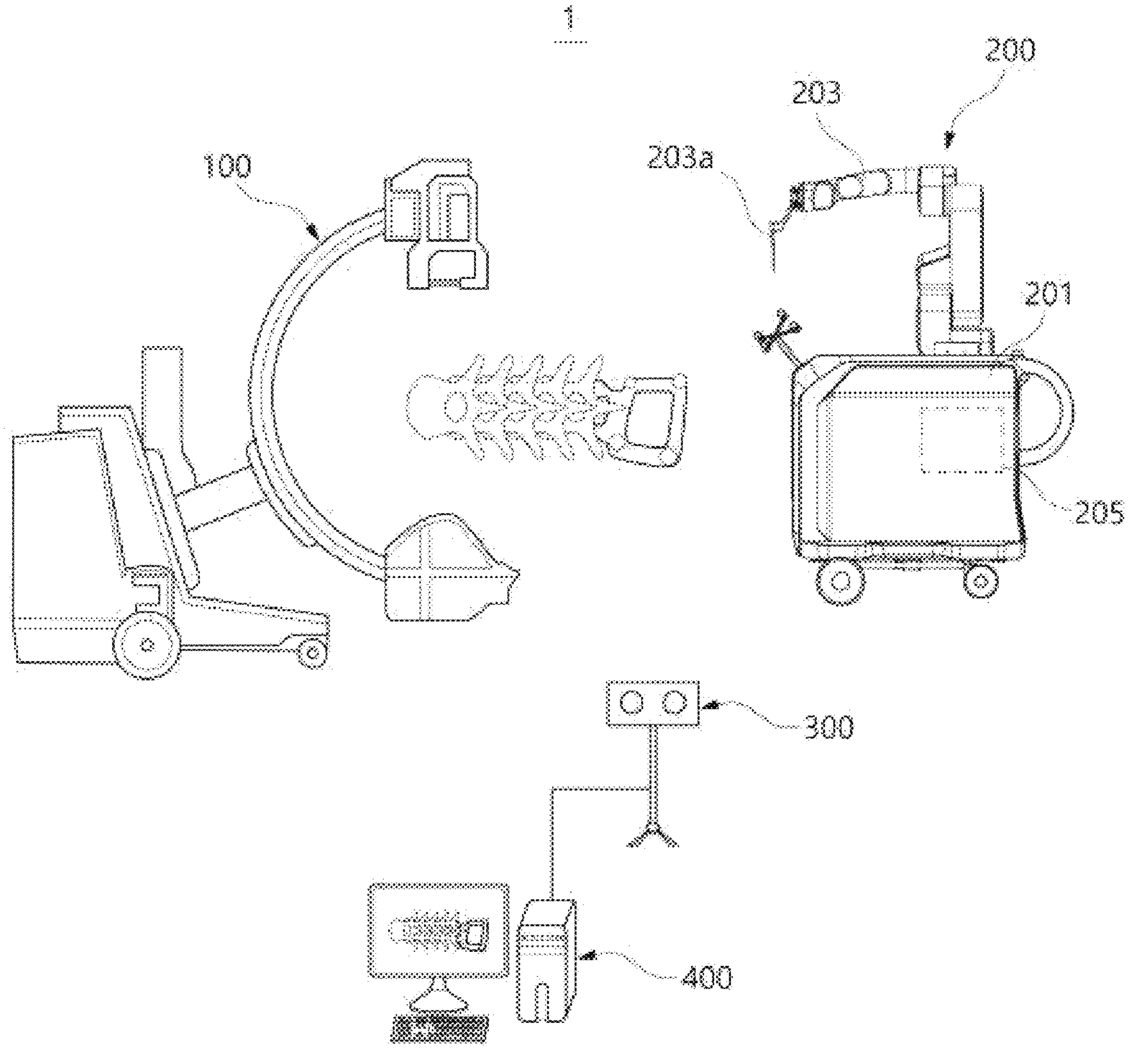
FIG. 19 is a schematic diagram of a medical operating robot system according to an embodiment of the disclosure.

Referring to FIG. 19, the medical operating robot system 1 according to an embodiment of the disclosure includes a C-arm imaging apparatus 100, a medical operating robot 200, a position sensor 300, and a navigation system 400, and the medical operating robot 200 includes a main body 201, a robot arm 203 with an end effector 203*a*, and a robot controller 205.

The C-arm imaging apparatus 100 is used to acquire the AP image and the LL image of a patient's surgical site during the operation.

The robot arm 203 is secured to the robot main body 201, and includes the end effector 203*a*, to which a surgical instrument is detachably coupled, at a distal end thereof. The position sensor 300 is implemented as an OTS that tracks the real-time position of the surgical instrument or the end effector 203*a* by recognizing the marker. The controller 205 is provided in the robot main body 201, and controls the robot arm 203 according to predetermined operation planning and control software.

The navigation system 400 performs the foregoing image registration method to display planning information about a surgical instrument or implant on a C-arm image acquired during an operation or display a real-time position of the surgical instrument or implant on the C-arm image or a 3D image acquired before the operation through a display, thereby assisting a doctor in performing the operation. To this end, the navigation system 400 may further include the display connected thereto so that a doctor can view the real-time position of the surgical instrument or the like as the operation plan and the operating status by his/her naked eyes during the operation. A person having ordinary knowledge in the art may easily understand that other elements than the navigation system 400 of FIG. 15 are the same as those commonly used in a medical operating robot system.

According to the disclosure, there is accurate and quick image registration processing which can compensate for movement due to rotation of a patient's body part Although embodiments of the disclosure have been described so far, it will be appreciated by those skilled in the art that modifications or substitutions may be made in all or part of the embodiments of the disclosure without departing from the technical spirit of the disclosure.

Accordingly, the foregoing embodiments are merely examples of the disclosure, and the scope of the disclosure falls into the appended claims and equivalents thereof.

What is claimed is:

1. An image registration method, steps of which are performed by an image registration apparatus comprising a processor, the method comprising:

acquiring a 3D image of a patient's surgical site from a 3D imaging apparatus before an operation;

extracting digitally reconstructed radiograph (DRR) images in an anterior-posterior (AP) direction and a lateral-lateral (LL) direction from the 3D image;

acquiring 2D images for an AP image and an LL image of the patient's surgical site from a 2D imaging apparatus during an operation;

determining, by the image registration apparatus, a first region of interest for each of the AP image and the LL image;

determining, by the image registration apparatus, a second region of interest corresponding to the first region of interest for each of the AP image and the LL image of the 2D images;

determining, by the image registration apparatus, a first volume of interest where planes intersect as a region of interest on the AP image and a region of interest on the LL image are moved in directions of first normal vectors for planes of the AP image and the LL image, from a geospatial relationship between a source and a detector for the DRR images;

determining, by the image registration apparatus, a second volume of interest where the planes intersect as the region of interest on the AP image and the region of interest on the LL image are moved in directions of second normal vectors for planes of the AP image and the LL image within a perspective projection relationship, wherein the geospatial relationship between the source and the detector for the 2D images comprises a perspective projection relationship;

determining a first rotation angle between a reference position and a first reference position of the patient's surgical site corresponding to the first reference position of the AP image or the LL image, based on a first rotation axis passing through a first origin and parallel to a cross product vector of the first normal vectors, from a geospatial relationship between the source and the detector with respect to the DRR images;

determining a second rotation angle between the reference position and a second reference position of the AP image or LL image corresponding to the reference position, based on a second rotation axis passing through a second origin and parallel to a cross product vector of the second normal vectors, from a geospatial relationship between the source and the detector with respect to the 2D images; and determining a transformation relationship between the 2D images and the DRR images based on the first rotation angle and the second rotation angle, from the geospatial relationship between sources and detectors of the DRR images and the 2D images, wherein the first reference position is positioned within the first region of interest, and the second reference position is positioned within the second region of interest, the first origin comprises a center of the first volume of interest, and the second origin comprises a center of the second volume of interest.

2. The method of claim 1, wherein the first reference position and the second reference position comprise a center of the AP image or the LL image for each of the 2D images and the DRR images, or a line or plane comprising the center.

3. The method of claim 1, further comprising performing operation planning based on the 3D image by the image registration apparatus, wherein the first origin for the DRR images is determined based on a relative relationship of a trajectory of a surgical instrument for mounting an implant or a mounting position of the implant applied to the operation planning.

4. The method of claim 1, wherein the reference position for the DRR images or the 2D images is determined based on a user's input.

5. The method of claim 1, wherein the geospatial relationship between the source and the detector for the DRR images comprises an orthogonal projection relationship, and the geospatial relationship between the source and the detector for the 2D images comprises the perspective projection relationship.

6. The method of claim 1, wherein each first region of interest for the AP image and the LL image of the DRR images comprises a rectangle, and regarding the DRR images, the method comprising:

a first step of calculating, by the image registration apparatus, first intersection points between an epipolar line on the LL image for vertices of the region of interest on the AP image and a midline connecting midpoints of an outer circumference or lateral sides of the region of interest on the LL image;

a second step of acquiring, by the image registration apparatus, four reconstructed points by orthogonal projection of the first intersection points to the normal vectors from the vertices of the region of interest on the AP image;

a third step of calculating, by the image registration apparatus, second intersection points between an epipolar line on the AP image for the vertices of the region of interest on the LL image and a midline connecting midpoints of an outer circumference or lateral sides of the region of interest on the AP image;

a fourth step of acquiring, by the image registration apparatus, four reconstructed points by orthogonal projection of the second intersection points to the normal vectors from the vertices of the region of interest on the LL image; and a fifth step of calculating, by the image registration apparatus, the first volume of interest in a hexahedron formed based on eight reconstructed points obtained through the first to fourth steps.

7. The method of claim 1, wherein the determining the second volume of interest comprises, regarding the 2D image, a first step of calculating, by the image registration apparatus, first intersection points between an epipolar line on the LL image for vertices of the region of interest on the AP image and a midline connecting midpoints of an outer circumference or lateral sides of the region of interest on the LL image;

a second step of acquiring, by the image registration apparatus, four reconstructed points by perspective projection of the first intersection points to perspective projection vectors from the vertices of the region of interest on the AP image toward the source;

a third step of calculating, by the image registration apparatus, second intersection points between an epipolar line on the AP image for the vertices of the region of interest on the LL image and a midline connecting midpoints of an outer circumference or lateral sides of the region of interest on the AP image;

a fourth step of acquiring, by the image registration apparatus, four reconstructed points by perspective projection of the second intersection points to the perspective projection vectors from the vertices of the region of interest on the LL image toward the source; and a fifth step of calculating, by the image registration apparatus, the second volume of interest in a hexahedron based on eight reconstructed points obtained through the first to fourth steps.

8. An image registration apparatus comprising a processor to perform the image registration method of claim 1.

9. A medical operating robot system comprising:

a 2D imaging apparatus configured to acquire a 2D image of a patient's surgical site during an operation;

a robot arm comprising an end effector to which a surgical instrument is detachably coupled;

a position sensor configured to detect a real-time position of the surgical instrument or the end effector;

a controller configured to control the robot arm based on predetermined operation planning;

a display; and a navigation system configured to display planning information about the surgical instrument or implant on the 2D image acquired during the operation or display the real-time position of the surgical instrument or an implant on the 2D image or a 3D image acquired before the operation, through the display, by performing the image registration method of claim 1.

10. A non-transitory computer-readable medium having stored thereon a program, when executed by a processor, causes the processor to perform the image registration method of claim 1.

11. An image registration method, steps of which are performed by an image registration apparatus comprising a processor, the method comprising:

acquiring a 3D image of a patient's surgical site from a 3D imaging apparatus before an operation;

extracting digitally reconstructed radiograph (DRR) images in an anterior-posterior (AP) direction and a lateral-lateral (LL) direction from the 3D image;

acquiring 2D images for an AP image and an LL image of the patient's surgical site from a 2D imaging apparatus during an operation;

determining a first region of interest for each of the AP image and the LL image of the DRR images;

determining a second region of interest corresponding to the first region of interest with respect to each of the AP image and the LL image of the 2D images;

determining a first volume of interest formed by intersection of planes upon parallel translation of a region of interest on the AP image and a region of interest on the LL image in a direction of a first normal vector to the planes of the AP image and the LL image, from a geospatial relationship between a source and a detector with respect to the DRR images;

determining a second volume of interest formed by intersection of planes upon translation of the region of interest on the AP image and the region of interest on the LL image in a direction of a second normal vector to the AP image and the LL image of the 2D images within a perspective projection range, wherein the geospatial relationship between the source and the detector for the 2D images comprises a perspective projection relationship;

determining first displacement between a first reference position within the first volume of interest corresponding to a predetermined first reference position in the first region of interest and a predetermined reference position corresponding to the first reference position;

determining second displacement between the predetermined reference position and a second reference position within the second volume of interest for a predetermined second reference position within the second region of interest corresponding to the predetermined reference position; and determining a transformation relationship to minimize a Euclidean distance between vertices of the first region of interest and vertices of the second region of interest based on a transformation relationship, as the transformation relationship between the 2D images and the DRR images is determined from geospatial relationships for the source and the detector of each of the DRR images and the 2D images, based on the first displacement and the second displacement.

12. The method of claim 11, wherein the determining the first displacement comprises determining a first rotation angle based on an angle between the predetermined reference position and the first reference position, with respect to a first rotation axis passing through a predetermined first origin and parallel to a cross product vector of first normal vectors for planes of the AP image and the LL image; and the determining the second displacement comprises determining a second rotation angle based on an angle between the predetermined reference position and the second reference position, with respect to a second rotation axis passing through a predetermined second origin and parallel to a cross product vector of the second normal vectors for planes of the AP image and the LL image.

13. The method of claim 11, wherein the determining the first volumes of interest and the second volumes of interest comprise forming a polyhedron by projecting an epipolar line of vertices of the first region of interest and the second region of interest to the first normal vectors and the second normal vectors.

* * * * *